US010994998B2

(12) United States Patent
Ehrenborg et al.

(10) Patent No.: US 10,994,998 B2
(45) Date of Patent: May 4, 2021

(54) SETTING OF HARDENABLE BONE SUBSTITUTE

(71) Applicant: BONE SUPPORT AB, Lund (SE)

(72) Inventors: Kristina Caroline Victoria Ehrenborg, Lund (SE); Veronica Rebecca Sandell, Bjärred (SE); Eva Christina Lidén, Lund (SE)

(73) Assignee: BONE SUPPORT AB, Lund (SE)

(*) Notice: Subject to any disclaimer, the term of this patent is extended or adjusted under 35 U.S.C. 154(b) by 401 days.

(21) Appl. No.: 15/981,501

(22) Filed: May 16, 2018

(65) Prior Publication Data
US 2018/0257939 A1    Sep. 13, 2018

Related U.S. Application Data

(62) Division of application No. 14/768,649, filed as application No. PCT/EP2014/053330 on Feb. 20, 2014, now Pat. No. 10,294,107.

(60) Provisional application No. 61/766,820, filed on Feb. 20, 2013.

(30) Foreign Application Priority Data

Feb. 20, 2013 (EP) ..................................... 13155895

(51) Int. Cl.
C01B 25/32      (2006.01)
A61L 27/12      (2006.01)
A61L 27/36      (2006.01)
A61K 9/14       (2006.01)
A61K 33/42      (2006.01)
A61K 31/7036    (2006.01)
A61K 33/06      (2006.01)
A61K 38/14      (2006.01)
A61L 27/54      (2006.01)
A61L 27/02      (2006.01)
A61K 9/00       (2006.01)
A61K 49/04      (2006.01)
A61L 27/10      (2006.01)

(52) U.S. Cl.
CPC .......... *C01B 25/327* (2013.01); *A61K 9/0024* (2013.01); *A61K 31/7036* (2013.01); *A61K 33/06* (2013.01); *A61K 33/42* (2013.01); *A61K 38/14* (2013.01); *A61K 49/04* (2013.01); *A61K 49/0433* (2013.01); *A61L 27/025* (2013.01); *A61L 27/10* (2013.01); *A61L 27/12* (2013.01); *A61L 27/365* (2013.01); *A61L 27/3608* (2013.01); *A61L 27/3616* (2013.01); *A61L 27/54* (2013.01); *A61L 2300/112* (2013.01); *A61L 2300/202* (2013.01); *A61L 2300/40* (2013.01); *A61L 2300/404* (2013.01); *A61L 2300/406* (2013.01); *A61L 2300/412* (2013.01); *A61L 2300/414* (2013.01); *A61L 2300/416* (2013.01); *A61L 2300/428* (2013.01); *A61L 2300/43* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| 949,163 | A | 2/1910 | Stapley |
| 1,644,173 | A | 10/1927 | Carr |
| 1,865,912 | A | 7/1932 | Horn |
| 2,545,017 | A | 3/1951 | Billingsley |
| 3,367,783 | A | 2/1968 | Billerbeck |
| 3,475,010 | A | 10/1969 | Cook et al. |
| 3,570,719 | A | 3/1971 | Schiff |
| 3,688,765 | A | 9/1972 | Gasaway |
| 3,837,379 | A | 9/1974 | McDonald et al. |
| 3,965,910 | A | 6/1976 | Fischer |
| 4,001,323 | A | 1/1977 | Felder et al. |
| 4,139,605 | A | 2/1979 | Felder et al. |
| 4,240,425 | A | 12/1980 | Akhavi |
| 4,269,331 | A | 5/1981 | Watson |
| 4,338,925 | A | 7/1982 | Miller |
| 4,348,377 | A | 9/1982 | Felder et al. |

(Continued)

FOREIGN PATENT DOCUMENTS

| CN | 1119832 | 4/1996 |
| CN | 101309708 | 11/2008 |

(Continued)

OTHER PUBLICATIONS

Ślósarczyk A, Czechowska J, Paszkiewicz Z, Zima A. New bone implant material with calcium sulfate and Ti modified hydroxyapatite. J Achiev Mater Manuf Eng. 2010;43(1):170-7. (Year: 2010).*
Patel N, Gibson IR, Ke S, Best SM, Bonfield W. Calcining influence on the powder properties of hydroxyapatite. Journal of Materials Science: Materials in Medicine. Feb. 1, 2001;12(2):181-8. (Year: 2001).*
Ruys AJ, Wei M, Sorrell CC, Dickson MR, Brandwood A, Milthorpe BK. Sintering effects on the strength of hydroxyapatite. Biomaterials. Jan. 1, 1995;16(5):409-15. (Year: 1995).*

(Continued)

*Primary Examiner* — Nissa M Westerberg
(74) *Attorney, Agent, or Firm* — Casimir Jones, S.C.; Anne M. Reynolds

(57) ABSTRACT

The invention relates to hardenable ceramic bone substitute compositions having improved setting, powders for such compositions and methods for their manufacture and use in medical treatment. More specifically the invention relates to hardenable bone substitute powder and hardenable bone substitute paste with improved setting properties, comprising calcium sulfate and heat-treated hydroxyapatite (passivated HA), which bone substitute is suitable for treatment of disorders of supportive tissue such as bone loss, bone fracture, bone trauma and osteomyelitis.

20 Claims, 4 Drawing Sheets

(56) References Cited

U.S. PATENT DOCUMENTS

Figure 1:
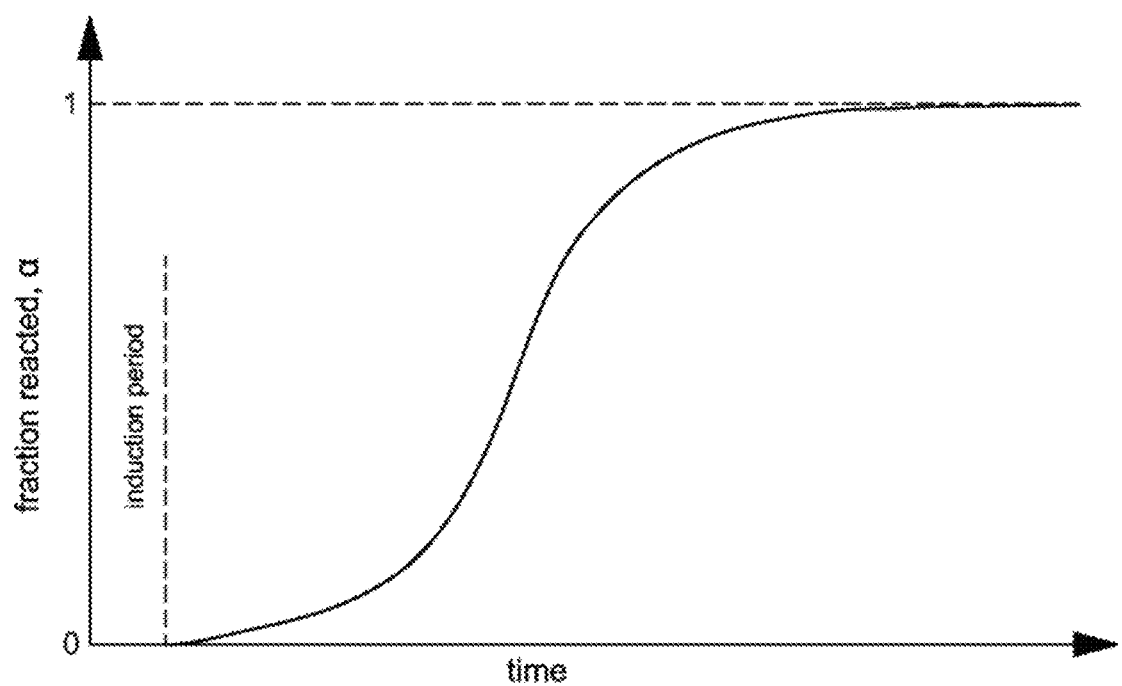

| | | |
|---|---|---|
| 4,487,766 A | 12/1984 | Mach |
| 4,496,342 A | 1/1985 | Banko |
| 4,518,430 A | 5/1985 | Brown et al. |
| 4,583,974 A | 4/1986 | Kokernak |
| 4,612,053 A | 9/1986 | Brown et al. |
| 4,619,655 A | 10/1986 | Hanker et al. |
| 4,673,296 A | 6/1987 | Sjogren |
| 4,676,655 A | 6/1987 | Handler |
| 4,721,390 A | 1/1988 | Lidgren |
| 4,752,479 A | 6/1988 | Briggs et al. |
| 4,832,500 A | 5/1989 | Brunold et al. |
| 4,994,442 A | 2/1991 | Gil et al. |
| 5,047,030 A | 9/1991 | Draenert |
| 5,071,040 A | 12/1991 | Laptewicz |
| 5,073,362 A | 12/1991 | Blaszkiewicz et al. |
| 5,149,368 A | 9/1992 | Liu et al. |
| 5,168,757 A | 12/1992 | Rabenau et al. |
| 5,232,024 A | 8/1993 | Williams |
| 5,252,301 A | 10/1993 | Nilson et al. |
| 5,262,166 A | 11/1993 | Liu et al. |
| 5,269,785 A | 12/1993 | Bonutti |
| 5,281,265 A | 1/1994 | Liu |
| 5,328,262 A | 7/1994 | Lidgren et al. |
| 5,328,462 A | 7/1994 | Fischer |
| 5,342,441 A | 8/1994 | Mandai et al. |
| 5,360,823 A | 11/1994 | Griffe, Jr. et al. |
| 5,403,318 A | 4/1995 | Boehringer et al. |
| 5,447,711 A | 9/1995 | Almen et al. |
| 5,462,722 A | 10/1995 | Liu et al. |
| 5,501,520 A | 3/1996 | Lidgren et al. |
| 5,549,380 A | 8/1996 | Lidgren et al. |
| 5,551,778 A | 9/1996 | Hauke et al. |
| 5,605,885 A | 2/1997 | Bernton et al. |
| 5,614,206 A | 3/1997 | Randolph et al. |
| 5,650,108 A | 7/1997 | Nies et al. |
| 5,665,066 A | 9/1997 | Fischer |
| 5,681,873 A | 10/1997 | Norton et al. |
| 5,695,742 A | 12/1997 | Felder et al. |
| 5,698,186 A | 12/1997 | Weeks |
| 5,756,127 A | 5/1998 | Grisoni |
| 5,766,247 A | 6/1998 | Aoki et al. |
| 5,797,873 A | 8/1998 | Franz et al. |
| 5,829,875 A | 11/1998 | Hagel et al. |
| 5,837,752 A | 11/1998 | Shastri et al. |
| 5,842,786 A | 12/1998 | Solomon |
| 5,866,100 A | 2/1999 | Tournier et al. |
| 5,871,549 A | 2/1999 | Jayashankar et al. |
| 5,891,423 A | 4/1999 | Weeks |
| 5,965,772 A | 10/1999 | Desantis |
| 5,997,544 A | 12/1999 | Nies et al. |
| 6,018,094 A | 1/2000 | Fox |
| 6,018,095 A | 1/2000 | Lerch et al. |
| 6,027,742 A | 2/2000 | Lee et al. |
| 6,062,722 A | 5/2000 | Lake |
| 6,071,982 A | 6/2000 | Wise et al. |
| 6,074,358 A | 6/2000 | Andrew et al. |
| 6,075,067 A | 6/2000 | Lidgren |
| 6,080,801 A | 6/2000 | Draenert et al. |
| 6,118,043 A | 9/2000 | Nies et al. |
| 6,120,174 A | 9/2000 | Haag et al. |
| 6,206,957 B1 | 3/2001 | Driessens et al. |
| 6,231,615 B1 | 5/2001 | Preissman |
| 6,248,110 B1 | 6/2001 | Reiley et al. |
| 6,251,139 B1 | 6/2001 | Lin et al. |
| 6,309,420 B1 | 10/2001 | Preissman |
| 6,365,218 B1 | 4/2002 | Borschel et al. |
| 6,367,962 B1 | 4/2002 | Mizutani et al. |
| 6,431,743 B1 | 8/2002 | Mizutani et al. |
| 6,440,138 B1 | 8/2002 | Reiley et al. |
| 6,447,809 B1 | 9/2002 | Krumhar et al. |
| 6,485,428 B1 | 11/2002 | Enk |
| 6,488,651 B1 | 12/2002 | Morris et al. |
| 6,586,009 B1 | 7/2003 | Lidgren |
| 6,596,904 B1 | 7/2003 | Dunn et al. |
| 6,689,375 B1 | 2/2004 | Wahlig et al. |
| 6,706,069 B2 | 3/2004 | Berger |
| 6,706,273 B1 | 3/2004 | Roessler |
| 6,716,216 B1 | 4/2004 | Boucher et al. |
| 6,719,761 B1 | 4/2004 | Reiley et al. |
| 6,723,334 B1 | 4/2004 | McGee et al. |
| 6,736,537 B2 | 5/2004 | Coffeen et al. |
| 6,740,090 B1 | 5/2004 | Cragg et al. |
| 6,897,339 B2 | 5/2005 | Turchetta et al. |
| 7,160,306 B2 | 1/2007 | Matsuzaki et al. |
| 7,393,342 B2 | 7/2008 | Henniges et al. |
| 7,393,405 B2 | 7/2008 | Bohner |
| 7,407,542 B2 | 8/2008 | Lemaitre et al. |
| 7,417,077 B2 | 8/2008 | Lidgren et al. |
| 7,524,103 B2 | 4/2009 | McGill et al. |
| 7,771,705 B2 | 8/2010 | Zhao |
| 7,972,630 B2 | 7/2011 | Lidgren |
| 8,420,127 B2 | 4/2013 | Lidgren et al. |
| 8,574,550 B2 | 11/2013 | Zhao |
| 2001/0012968 A1 | 8/2001 | Preissman |
| 2001/0051670 A1 | 12/2001 | Goupil et al. |
| 2002/0055143 A1 | 5/2002 | Bell et al. |
| 2002/0076378 A1 | 6/2002 | Wolfe et al. |
| 2002/0101785 A1 | 8/2002 | Edwards et al. |
| 2002/0156483 A1 | 10/2002 | Voellmicke et al. |
| 2002/0169506 A1 | 11/2002 | Matsushima et al. |
| 2003/0018339 A1 | 1/2003 | Higueras et al. |
| 2003/0028251 A1 | 2/2003 | Mathews |
| 2003/0040718 A1 | 2/2003 | Kust et al. |
| 2003/0049329 A1 | 3/2003 | Lee et al. |
| 2003/0050702 A1 | 3/2003 | Berger |
| 2003/0055512 A1 | 3/2003 | Genin et al. |
| 2003/0109883 A1 | 6/2003 | Matsuzaki et al. |
| 2003/0161858 A1 | 8/2003 | Lidgren |
| 2003/0181986 A1 | 9/2003 | Buchholz |
| 2004/0006347 A1 | 1/2004 | Sproul |
| 2004/0048947 A1* | 3/2004 | Lidgren ............... A61P 11/00 523/116 |
| 2004/0049202 A1 | 3/2004 | Berger |
| 2004/0068234 A1 | 4/2004 | Martin et al. |
| 2004/0068266 A1 | 4/2004 | Delmotte |
| 2004/0137032 A1 | 7/2004 | Wang |
| 2004/0151751 A1 | 8/2004 | Cooper |
| 2004/0191897 A1 | 9/2004 | Muschler |
| 2004/0244651 A1 | 12/2004 | Lemaitre et al. |
| 2005/0015074 A1 | 1/2005 | Trombley |
| 2005/0023171 A1 | 2/2005 | Delaney et al. |
| 2005/0105385 A1 | 5/2005 | McGill et al. |
| 2005/0119746 A1 | 6/2005 | Lidgren |
| 2005/0128868 A1 | 6/2005 | Vries |
| 2005/0197629 A1 | 9/2005 | Conway |
| 2005/0241535 A1 | 11/2005 | Bohner |
| 2005/0251149 A1 | 11/2005 | Wenz |
| 2005/0257714 A1 | 11/2005 | Constantz et al. |
| 2005/0287071 A1 | 12/2005 | Wenz |
| 2006/0004358 A1 | 1/2006 | Serhan et al. |
| 2006/0036211 A1 | 2/2006 | Solsberg et al. |
| 2006/0041033 A1 | 2/2006 | Bisig et al. |
| 2006/0122621 A1 | 6/2006 | Truckai et al. |
| 2007/0041906 A1* | 2/2007 | Lidgren ............... A61K 33/06 424/9.4 |
| 2007/0161943 A1 | 7/2007 | Lidgren et al. |
| 2007/0217282 A1 | 9/2007 | Lidgren et al. |
| 2008/0065088 A1 | 3/2008 | Hughes et al. |
| 2008/0096797 A1 | 4/2008 | Li et al. |
| 2008/0161752 A1 | 7/2008 | Rajala et al. |
| 2008/0208354 A1 | 8/2008 | Bohner |
| 2008/0318862 A1 | 12/2008 | Ashman et al. |
| 2010/0249753 A1 | 9/2010 | Gaisser et al. |

FOREIGN PATENT DOCUMENTS

| | | |
|---|---|---|
| DE | 44 09 610 | 9/1995 |
| DE | 202 16 632 | 3/2004 |
| EP | 0 023 992 | 2/1981 |
| EP | 0 109 310 | 5/1984 |
| EP | 0 308 364 | 3/1989 |
| EP | 0 495 284 | 7/1992 |
| EP | 0 639 382 | 2/1995 |
| EP | 0 657 208 | 6/1995 |

(56) References Cited

FOREIGN PATENT DOCUMENTS

| | | |
|---|---|---|
| EP | 0 520 690 | 11/1995 |
| EP | 0 807 432 | 11/1997 |
| EP | 0 835 668 | 4/1998 |
| EP | 0 950 420 | 10/1999 |
| EP | 1 002 513 | 5/2000 |
| EP | 1 155 704 | 11/2001 |
| EP | 1 296 909 | 1/2002 |
| EP | 1 208 850 | 5/2002 |
| EP | 0 639 382 | 7/2002 |
| EP | 1 132 061 | 8/2004 |
| EP | 1610832 B1 | 1/2006 |
| EP | 1712244 | 10/2006 |
| EP | 1891984 | 2/2008 |
| EP | 2660267 | 11/2013 |
| ES | 2 178 556 | 12/2002 |
| GB | 2 239 818 | 7/1991 |
| GB | 2 338 428 | 12/1999 |
| JP | 64-22256 | 1/1989 |
| JP | 64-22257 | 1/1989 |
| JP | 1-139516 | 6/1989 |
| JP | H04265214 | 9/1992 |
| JP | 5-168692 | 7/1993 |
| JP | 5-507862 | 11/1993 |
| JP | 9-502368 | 3/1997 |
| JP | 2935708 | 8/1999 |
| JP | 2000-000295 | 1/2000 |
| JP | 2000-159564 | 6/2000 |
| JP | 2001-106638 | 4/2001 |
| JP | 2001-510078 | 7/2001 |
| JP | 2001-517997 | 10/2001 |
| JP | 2002-058736 | 2/2002 |
| JP | 2002-325831 | 11/2002 |
| JP | 2003-507090 | 2/2003 |
| SE | 8903538 | 4/1991 |
| WO | WO 85/01727 | 4/1985 |
| WO | WO 87/05521 | 9/1987 |
| WO | WO 88/06023 | 8/1988 |
| WO | WO 89/03695 | 5/1989 |
| WO | WO 91/00252 | 1/1991 |
| WO | WO 91/17722 | 11/1991 |
| WO | WO 93/14799 | 8/1993 |
| WO | WO 95/07108 | 3/1995 |
| WO | WO 96/14265 | 5/1996 |
| WO | WO 96/39202 | 12/1996 |
| WO | WO 97/38676 | 10/1997 |
| WO | WO 97/47334 | 12/1997 |
| WO | WO 99/17710 | 4/1999 |
| WO | WO 99/62570 | 12/1999 |
| WO | WO 99/65597 | 12/1999 |
| WO | WO 00/02597 | 1/2000 |
| WO | WO 00/26179 | 5/2000 |
| WO | WO 00/45867 | 8/2000 |
| WO | WO 01/34216 | 5/2001 |
| WO | WO 01/76649 | 10/2001 |
| WO | WO 02/05861 | 1/2002 |
| WO | WO 02/058755 | 8/2002 |
| WO | WO 02/080933 | 10/2002 |
| WO | WO 03/011957 | 2/2003 |
| WO | WO 03/037165 | 5/2003 |
| WO | WO 03/041753 | 5/2003 |
| WO | WO 03/053488 | 7/2003 |
| WO | WO 2003/053488 | 7/2003 |
| WO | WO 2004/000374 | 12/2003 |
| WO | WO 2004/002615 | 1/2004 |
| WO | WO 2004/026377 | 4/2004 |
| WO | WO 2004/050131 | 6/2004 |
| WO | WO 2004/078223 | 9/2004 |
| WO | WO 2004/087229 | 10/2004 |
| WO | WO 2004/091435 | 10/2004 |
| WO | WO 2005/099783 | 10/2005 |
| WO | WO 2005/122971 | 12/2005 |
| WO | WO 2006/015316 | 2/2006 |
| WO | WO 2006/041365 | 4/2006 |
| WO | WO 2006/118461 | 11/2006 |
| WO | WO 2007/143698 | 12/2007 |
| WO | WO 2008/023254 | 2/2008 |
| WO | WO 2009/081169 | 7/2009 |
| WO | WO 2009/132466 | 11/2009 |
| WO | WO 2011/098438 | 8/2011 |

OTHER PUBLICATIONS

"Powder (substance)," http://en.wikipedia.org/wiki/Powder_(substance) (last visited Dec. 1, 2008).
Aebli, N. et al., "Cardiovascular Changes During Multiple Vertebroplasty With and Without Vent-Hole," SPINE (2003) 28(14):1504-1512.
Barbalace, K.L., "Chemical Database: Calcium Sulfate," Environmental Chemistry.com, http://envionmentalchemistry.com/yogi/chemicals/cn/Calcium%AOsulfate.html (last visited Feb. 5, 2009).
Bohner, M. et al., "Effects of Sulfate Ions on the in Vitro Properties of l1-TCP—MCPM—Water Mixtures. Preliminary In Vivo Results," Bioceramics (1995) 48:245-259.
Bohner, M. et al., "New Hydraulic Cements Based on a-Tricalcium Phosphate—Calcium Sulfate Dihydrate Mixtures," Biomaterials (2004) 25:741-749.
Bohner et al., "A physical approach to modify the hydraulic reactivity of alpha-tricalcium phosphate powder." Acta Biomater. Nov. 2009; 5(9):3524-35.
Bohner, M., "Physical and Chemical Aspects of Calcium Phosphates Used in Spinal Surgery," Eur. SpineJ. (2001) 10:S114-S121.
Cabanas, M.V. et al., "Setting Behavior and in Vitro Bioactivity of Hydroxyapatite/Calcium Sulfate Cements," Chern. Mater. (2002) 14(8):3550-3555.
Cahn, R.W. et al. eds., "Materials Science and Technology: A Comprehensive Treatment," Medical and Dental Materials (1992) 14:70-72, 101-109.
Chinese Patent Office Action for Application No. 201480009462.8 dated Jun. 24, 2016 (19 pages including translation).
Damien, C.J. et al., "Student Research Award in the Graduate Degree Candidate Category, 16th Annual Meeting of the Society for Biomaterials, Charleston, SC, May 20-23, 1990: Investigation of a Hydroxyapatite and Calcium Sulfate Composition Supplement with an Osteoinductive Factor," J. Biomedical Materials Research (1990) 24:639-654.
Engqvist, H. et al., "Chemical Stability of a Novel Injectable Bioceramic for Stabilisation of Vertebral Compression Fractures," Trends Biomater. Artif. Organs (2008) 21(2):98-106.
Eromosele, C.O. et al. "Characterization and Viscosity Parameters of Seed Oils from Wild Plants," Bioresource Technology (2002) 86(2):203-205.
Gitelis, S. et al., "The Treatment of Chronic Osteomyelitis with a Biodegradable Antibiotic-Impregnated Implant," J. Orthopaedic Surgery (2002) 10(1):53-60.
Ima-Nirwana, S. et al., "Palm Vitamin E Improves Bone Metabolism and Survival Rate in Thyrotoxic Rats," Gen. Pharmacal. (1999) 32:621-626.
Japanese Patent Office Action for Application No. 2015-557483 dated Dec. 19, 2017 (9 pages, English translation included).
Karr, J. C. "Management of a Diabetic Patient Presenting with Forefoot Osteomyelitis: The Use of Cerament Bone Void Filler Impregnated with Vancomycin—An Off Label Use," J. Diabetic Foot Complications (2009) 1(4):94-100.
Karr, J. "Osteomyelitis and Antibiotic Beads—What Do You Think About Using Antibiotics Other than Vancomycin or Aminoglycosides?," (Aug. 22, 2009, 7:23PM), http://www.podiatry.com/etalk/Osteomyelitis-and-antibiotic-t1045.html (retrieved Nov. 4, 2012).
Kirby, B.S. et al., "Acute Bronchospasm Due to Exposure to Polymethylmethacrylate Vapors During Percutaneous Vertebroplasty," AJR (2003) 180:543-544.
Koessler, M.J. et al., "Fat a.nd Bone Marrow Embolism During Percutaneous Vertebroplasty," Anesth. Ana/g. (2003) 97:293-294.
Komath, M. et al., "On the Development of an Apatitic Calcium Phosphate Bone Cement," Bull. Mater. Sci. (2000) 23(2):135-140.
Lei, D. et al., "Mechanical Properties of Calcium Sulphate/Hydroxyapatite Cement," Bio-Medical Materials & Engineering (2006) 16:423-428.

(56) References Cited

OTHER PUBLICATIONS

Lidgren, L., "Bone Substitutes," Karger Gazette: No. 65 Bone & Joints (2002) 65:1-4.
Liu, D. et al., "Augmentation of Pedicle Screw Stability with Calcium Sulfate Cement in Osteoporotic Sheep," J. Spinal Disord Tech (2011) 24(4):235-241.
Mirtchi, A.A. et al., "Calcium Phosphate Cements: Action of Setting Regulators on the Properties of the 11-Tricalcium Phosphate-Monocalcium Phosphate Cements," Biomaterials (1989) 10(9):634-638.
Nilsson, M. et al., "Biodegradation and Biocompatability of a Calcium Sulphate-Hydroxyapatite Bone Substitute," J. of Bone & Joint Surgery [Br] (2004) 86-B:120-125.
Nilsson,M. et al., "Characterization of a Novel Calcium Phosphate/ Sulphate Bone Cement," J. Biomedical Materials Research (2002) 61(4):600-607.
Nilsson, M. et al., "New Perspectives of Bioactives Calcium Phosphate Cements for Biomedical Applications," Research Centre in Biomedical Engineering, Dept. of Material Science and Metallurgy, Universitat Politecnica de Catalunya, Avda. Diagonal 647, Barcelona, E-08028, Spain, pp. 95-99, Nov. 2000.
Nilsson, M. et al., "The Effect of Aging an Injectable Bone Graft Substitute in Simulated Body Fluid," Key Engineering Materials (2003) 240-242:403-406.
Parsons, J.R. et al., "Osteoconductive Composite Grouts for Orthopedic Use," annals New York Academy of Sciences (1988) 523: 190-207.
Raynaud, S. et al., "Calcium phosphate apatites with variable Ca/P atomic ratio I. Synthesis, characterisation and thermal stability of powders," Biomaterials, vol. 23, 2002, pp. 1065-1080.
Richelsoph, K.C. et al., "Elution Behavior of Daptomycin-Loaded Calcium Sulfate Pellets," Clin. Orthopaedics & Related Res. (2007) 461:68-73.
Rodriguez-Lorenzo et al., "Fabrication of hydroxyapatite bodies by uniaxial pressing from a precipitated powder," Biomaterials 22 (2001) 583-588.
Singh, N.B. et al., "Calcium Sulphate Hemihydrate Hydration Leading to Gypsum Crystallization," Prog. Crystal Growth & Characterization of Materials (2007) 53:57-77.
Starling, S., "EFSA Says Calcium Sulphate Safe in Supplements," (Oct. 10, 2008), www.nutraingredients.com/Regulation/EFSA-says-calcium-sulphate-safe-in-supplements (last visited Feb. 5, 2009).
Technical Specification, Calcium Sulfate Hemihydrate Food Grade, 2009.
Yi, X. et al. "Augmentation of Pedicle Screw Fixation Strength Using an Injectable Calcium Sulfate Cement," SPINE (2008) 33(23):2503-2509.
Zampelis, V. et al., "The Effect of a Biphasic Injectable Bone Substitute on the Interface Strength in a Rabbit Knee Prosthesis Model," J. Orthopaedic Surgery & Research (2013) 8(25).
International Preliminary Examination Report for PCT/SE01/01627 dated Oct. 14, 2002, 11 pages.
International Preliminary Examination Report for PCT/SE02/02428 dated Mar. 16, 2004, 11 pages.
International Preliminary Report on Patentability for PCT/SE2004/ 000328 dated Aug. 30, 2005, 8 pages.
International Preliminary Report on Patentability for PCT/SE2004/ 001626 dated Feb. 13, 2006, 5 pages.
International Preliminary Report on Patentability for PCT/SE2005/ 000932 dated Dec. 28, 2006, 5 pages.
International Search Report for PCT/SE01/00789 dated Jul. 9, 2001, 2 pages.
International Search Report for PCT/SE01/01627 dated Dec. 18, 2001, 2 pages.
International Search Report for PCT/SE02/02428 dated Apr. 4, 2003, 4 pages.
International Search Report for PCT/SE2004/000328 dated Jun. 8, 2004, 6 pages.
International Search Report for PCT/SE2004/001626 dated Feb. 28, 2005, 4 pages.
International Search Report for PCT/SE2005/000932 dated Oct. 10, 2005, 3 pages.
File History for related U.S. Appl. No. 10/257,561, filed Mar. 11, 2003.
File History for related U.S. Appl. No. 10/333,026, filed Oct. 22, 2003.
File History for related U.S. Appl. No. 10/499,023, filed Feb. 8, 2005.
File History for related U.S. Appl. No. 10/547,671, filed Oct. 16, 2006.
File History for related U.S. Appl. No. 10/578,734, filed May 10, 2006.
File History for related U.S. Appl. No. 11/587,313, filed Oct. 23, 2006.
File History for related U.S. Appl. No. 12/122,873, filed May 19, 2008.
File History for related U.S. Appl. No. 12/219,542, filed Jul. 23, 2008.
File History for related U.S. Appl. No. 12/219,543, filed Jul. 23, 2008.
File History for related U.S. Appl. No. 12/585,194, filed Sep. 8, 2009.
File History for related U.S. Appl. No. 13/022,771, filed Feb. 8, 2011.
File History for related U.S. Appl. No. 13/613,563, filed Sep. 13, 2012.
File History for related U.S. Appl. No. 13/799,959, filed Mar. 13, 2013.
File History for related U.S. Appl. No. 14/157,304, filed Jan. 16, 2014.
Office Action for JP2006-539432, dated Jun. 1, 2010, 12 pages, English Translation.
Office Action for JP2003-554244, dated Jun. 2, 2009, 5 pages, English Translation.
Office Action for JP2006-507949, dated Sep. 14, 2010, 4 pages, English Translation.
Office Action for JP2002-511792, dated Oct. 3, 2011, 8 pages, English Translation.
Acarturk, O. et al., "Bone Healing Response to an Injectable Calcium Phosphate Cement With Enhanced Radiopacity" J Biomed Mat Res Part B: Appl Biomater 56-62, 2008.
Aunoble, S. et al., "Biological performance of a new •—TCP/PLLA composite material for applications in spine surgery: In vitro and in vivo studies" J Biomed Mat Res 78A: 416-422, 2006.
Dorozhkin, S., "Calcium orthophosphate cements for biomedical applications", J Mater Sci (2008) 43: 3028-3057.
Gitelis, et al: The treatment of chronic osteomyelitis with a biodegradable antibiotic-impregnated implant. Journal of Orthopaedic Surgery, 2002, 10(1): 53-60, XP002590798.
Habraken, W et al., "Ceramic composites as matrices and scaffolds for drug delivery in tissue engineering", Advanced Drug Delivery Reviews 59 (2007) 234-248.
Habraken, W et al., Introduction of enzymatically degradable poly(trimethylene carbonate) microspheres into an injectable calcium phosphate cement, Biomaterials 29, 2008, 2464-2476.
Habraken, W et al., "Introduction of gelatin microspheres into an injectable calcium phosphate cement", J Biomed Mater Res 87A: 643-655, 2008.
Kikuchi, M et al., "In vitro change in mechanical strength of •—tricalcium phosphate/copolymerized poly-L-lactide composites and their application for guided bone regeneration", J Biomed Mat Res 62, 2002, 265-272.
Lewis, G., "Injectable Bone Cements for Use in Vertebroplasty and Kyphoplasty: State-of-the-Art Review". J Biomed Mater Res Part B: Appl Biomater 76B: 456-468, 2006.
Lin, L et al., "Preparation and Evaluation of •—TCP/PLLA Microspheres as Osteogenesis Materials", J Appl Polym Sci 108:3210-3217, 2008.
Link, D et al., "Bone response and mechanical strength of rabbit femoral defects filled with injectable CaP cements containing TGF-• 1 loaded gelatine microparticles", Biomaterials 29 (2008), 675-682.

(56) References Cited

OTHER PUBLICATIONS

Link, D et al., "Evaluation of the biocompatibility of calcium phosphate cement/PLGA microparticle composites", J Biomed Mater Res 87A: 760-769, 2008.

M. V. Cabanas et al: Setting Behaviour and in Vitro Bioactivity of Hydroxyapatite/Calcium Sulfate Cements. Chemistry of Materials, vol. 14, No. 8, Aug. 1, 2002, pp. 3550-3555, XP055072711.

N. B. Singh and B. Middendorf "Calcium sulfate hemihydrate hydration leading to gypsum crystallization" Progress in Crystal Growth and Characteriation of Materials 53 (2007) 57-77.

Rezwan et al., "Biodegradable and bioactive porous polymer/inorganic composite scaffolds for bone tissue engineering" Biomaterials 27 (2006) 3413-3431.

Ruhe, Petal., "Biocompability and degradation of poly(DL-lactic-co-glycolic acid)/calcium phosphate cement composites", J Biomed Mat Res 7aA: 533-544, 2006.

Ruhe, Petal., "Porous Poly(DL-lactic-co-glycolic acid)/Calcium Phosphate Cement Composite for Reconstruction of Bone Defects", Tissue Engineering vol. 12, No. 4, 2006, 789-800.

Vlad, M. D. et al., "Effect of the calcium to phosphorus ratio on the setting properties of calcium phosphate bone cements." Journal of Materials Science: Materials in Medicine 23.9 (2012): 2081-2090. (2012).

Ruksudjarit, A., et al. "Synthesis and characterization of nanocrystalline hydroxyapatite from natural bovine bone." Current applied physics 8.3 (2008): 270-272.

Ruys, A. J., et al. "Sinistering effects on the strength of hydroxyapatite." Biomaterials 16.5 (1995): 409-415.

Patel, N., et al. "Calcining influence on the powder properties of hydroxyapatite." Journal of Materials Science: Materials in Medicine 12.2 (2001): 181-188.

Guo, Linghong et al. "Effects of sintering temperature on structure of hydroxyapatite studied with Rietveld method." Journal of Materials Science: Materials in Medicine 14.9 (2003): 817-822.

* cited by examiner

SETTING OF HARDENABLE BONE SUBSTITUTE

This is a continuation of U.S. patent application Ser. No. 14/768,649, filed on Aug. 18, 2015, now U.S. Pat. No. 10,294,107, issued on May 21, 2019, which is a U.S. national stage entry of International Patent Application No. PCT/EP2014/053330, filed on Feb. 20, 2014, which claims priority to European Patent Application No. 13155895.9, filed on Feb. 20, 2013, and to U.S. Application No. 61/766,820, filed on Feb. 20, 2013, the entire contents of all of which are fully incorporated herein by reference.

FIELD OF THE INVENTION

The present invention relates to hardenable ceramic bone substitute compositions having improved setting, powders for such compositions and methods for their manufacture and use in medical treatment. More specifically the invention relates to hardenable bone substitute powder and hardenable bone substitute paste with improved setting properties, comprising calcium sulfate and heat-treated hydroxyapatite (passivated HA), which bone substitute is suitable for treatment of disorders of supportive tissue such as bone loss, bone fracture, bone trauma and osteomyelitis.

BACKGROUND OF THE INVENTION

Bone is the second most common tissue to be transplanted after blood. The most reliable method to repair bone defects is to use autogenous bone, i.e. bone taken from another site in the body. However, problems may occur at the second surgical site from where the graft is taken. To avoid this extra trauma, allografts can be used, i.e. bone graft between individuals of the same species. Allografts have a lower osteogenic capacity than autografts and the rate of new bone formation might be lower. They also have a higher resorption rate, a larger immunogenic response and less revascularisation of the recipient. Allografts must also be controlled for viruses since they can transfer, for example, HIV and hepatitis. The use of allografts is now the most common method for bone transplantation and repairing of bone defects. To solve the problems of supply, unpredictable strength and risk of infection, synthetic bone substitutes have become a realistic alternative. Thus, the demand for and use of synthetic bone substitutes is increasing rapidly.

Ceramic based synthetic bones substitutes can be divided into two main types. One type is based on calcium phosphate as the setting component and these are referred to as calcium phosphate cements. Another type is based on calcium sulfate as the setting component. The most important advantage with calcium sulfate is its excellent biocompatibility. The drawbacks with pure calcium sulfate bone substitutes are the rapid resorption and low strength, which make them less useful in larger or non-contained defects and when the fracture healing exceeds 4-6 weeks.

Bone Support AB has developed hardenable and injectable calcium sulfate based bone substitutes with the powder phase comprising approximately 40 wt % sintered hydroxyapatite (HA) ($Ca_{10}(PO_4)_6(OH)_2$) and approximately 60 wt % calcium sulfate hemihydrate, CSH, ($CaSO_4 \cdot \frac{1}{2} H_2O$). Of the two components, only CSH will set during the setting process. The HA powder will remain un-dissolved. The liquid phase of the injectable paste consists of an aqueous solution that for some of the products contain iohexol molecules to enhance the radiopacity of the material (WO2003/053488). If only the calcium sulfate was present in the bone substitute, there would be a complete material resorption within approximately 4-6 weeks. However, since there is also HA in the sample, this will slow down the calcium sulfate resorption. In addition, the HA in the sample will remain at the site of implantation for a longer time due to its high crystallinity and low solubility.

The setting time of the hardened bone substitute from the paste is an important parameter for determining their applicability as bone substitutes. Gillmore needles (ASTM C266) are often used to measure the initial setting time (IST) and the final setting time (FST) of cements. In a clinical situation the IST and FST can be interpreted such that the cement should be implanted before IST is reached and the wound is ready to be closed after the FST. IST times around 5-25 min typically allows sufficient time for the cement to be injected or molded, and FST times around 10-40 minutes are usually acceptable for clinical use. It is preferred to have IST times around 5-15 minutes, such as less than 10 minutes. Different products have different specifications since they will be used for different applications. Other ways of determining the applicability of a hardenable bone substitute are known in the art.

For a variety of applications, it is desirable to be able to mix different additives with bone substitutes, where calcium sulfate is a setting component. Bone substitutes comprising an additive such as for example an antibiotic would be desirable to have in order to be able to treat or prevent different disorders, e.g. osteomyelitis (bone infections). However, it has been found that the addition of some bioactive agents, such as antibiotics, retard the setting of the bone substitute in such a manner that the setting time exceeds clinically acceptable values. It has also been found that not only additives, but also basic components of the bone substitute, such as HA, may have a negative effect on the setting properties. It has surprisingly turned out, that the rate of the CSH hydration necessary for setting of the calcium sulfate in a HA containing calcium sulfate based bone substitute is highly dependent on the properties of the HA.

SUMMARY OF THE INVENTION

The present invention was made in view of the problems observed in connection with the prior art described above, and the object of the present invention has been to provide a solution to the problem which solution is the provision of a HA that does not, alone or together with different additives such as antibiotics, give clinically poor and/or unacceptable setting times for hardenable bone substitutes based on calcium sulfate (CSH) and hydroxyapatite (HA).

When CSH is mixed with water, it will hydrate to calcium sulfate dihydrate (CSD) according to the below reaction scheme (1):

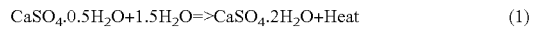

$$CaSO_4 \cdot 0.5H_2O + 1.5H_2O => CaSO_4 \cdot 2H_2O + Heat \qquad (1)$$

The hydration reaction of CSH can be summarized in three phases (N. B. Singh and B. Middendorf, *Calcium sulfate hemihydrate hydration leading to gypsum crystallization*, Progress in Crystal Growth and Characterization of Materials 53 (2007) 57-77):

1) The induction period starts immediately after the CSH powder is mixed with water. The CSH dissolves and the solution becomes supersaturated with respect to calcium and sulfate ions. This leads to precipitation of the less soluble calcium sulfate dihydrate (CSD). In order for the hydration reaction to be able to proceed, initially formed CSD nucleuses need to have a radius that is larger than a "critical radius" (to be determined for each specific system). The induction period is critical for the hydration reaction and any disturbances in the solubility of CSH or growth of CSD crystals in this phase will delay the further hydration reaction to a higher degree than if the same disturbances took place in a later phase of the process.

2) The acceleration or growth period starts when a sufficient number of CSD crystals have reached the critical size for acting as nucleating embryos. The CSD nucleus formed will then grow and form large crystals. The crystals will eventually be sufficiently large to interlock with each other and the friction between crystals contributes to the strength of the formed solidified material.

3) The third phase is relatively slow and consists of the completion of the hydration of the CSH as illustrated in FIG. 1 in the form of a schematic view showing the fraction of hydrated calcium sulfate as a function of time.

The inventors of the present invention have surprisingly found that the unpredictable setting properties of hardenable bone substitutes comprising CSH and HA (example 1) which most often lead to clinically unacceptable setting times, can be overcome by making the HA practically inert to the CSH hydration reaction by exposing sintered and micronized HA powder ("raw HA powder"), normally used in hardenable bone substitutes, to a heat-treatment step of for example 500° C. for two hours, where temperature and time are inversely related, to obtain "passivated HA powder" (pHA). The negative effect of the raw HA on the setting of the calcium sulfate in hardenable bone substitutes can be significantly lowered when sintered and micronized raw HA ("raw HA powder"), e.g. commercially available hydroxyapatite, is heat-treated before use. The decrease in retardation of the setting time is seen when the HA powder (raw or passivated) is mixed with CSH alone but in particular when it is mixed with CSH in combination with further components in form of additive, such as antibiotics. This heat-treatment to make sintered and micronized raw HA practically inert is denoted "passivation" throughout this document and sintered and micronized HA that has undergone heat-treatment will be described as "passivated HA" (pHA).

Another advantage of passivating HA is that the setting of a hardenable bone substitute will become more reliable and kept under control without changing the composition of the bone substitute by adding further chemicals, such as accelerants. With the present invention, it is not necessary to apply special procedures when adding additives, such as for example antibiotics, to the hardenable bone substitute. This can be seen as an improvement over previous attempts made by Bone Support AB to prevent undesirable prolonged setting times by allowing the hydration reaction of CSH to start before adding any other additives, such as antibiotics, to the bone substitute in its paste form (WO 2011/098438).

The passivated HA is also shown to be more resistant to storage over time and to changing temperatures and relative humidity in the surroundings of stored hardenable bone substitute products (see Example 12). In addition, setting time for hardenable bone substitutes containing different lots of passivated HA but with the same CSH/HA ratio have become much more uniform than when using non-passivated raw HA, and thus much more predictable. The minimized spread in setting times is surprisingly also independent of the degree of retardation induced by the same raw HA lots before passivation.

Hydroxyapatite

Raw HA can be produced in several ways. The most common way to synthesize HA is by wet precipitation methods using orthophosphoric acid and calcium hydroxide as raw materials followed by drying and heating.

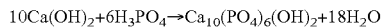

It has been seen that the morphology and size of the precipitated particles change in each stage of the process. After drying, the nanoparticles tend to form small agglomerates.

HA can also be produced with a solid state reaction where the $Ca^{2+}$ and $PO_4^{3-}$ are mixed dry and then heated to a high temperature. In order to mix $Ca^{2+}$ and $PO_4^{3-}$, several combinations of salts can be mixed. By using different salt combinations, a lot of different precipitation/solid state reaction can be performed.

Regardless of how HA is produced, $Ca^{2+}$ is mixed with $PO_4^{3-}$ in a ratio of 1.67. If HA is to be precipitated, the $Ca^{2+}$ and the $PO_4^{3-}$ are added to a water solution and the pH and temperature is controlled while the HA is precipitated.

Figure 4:
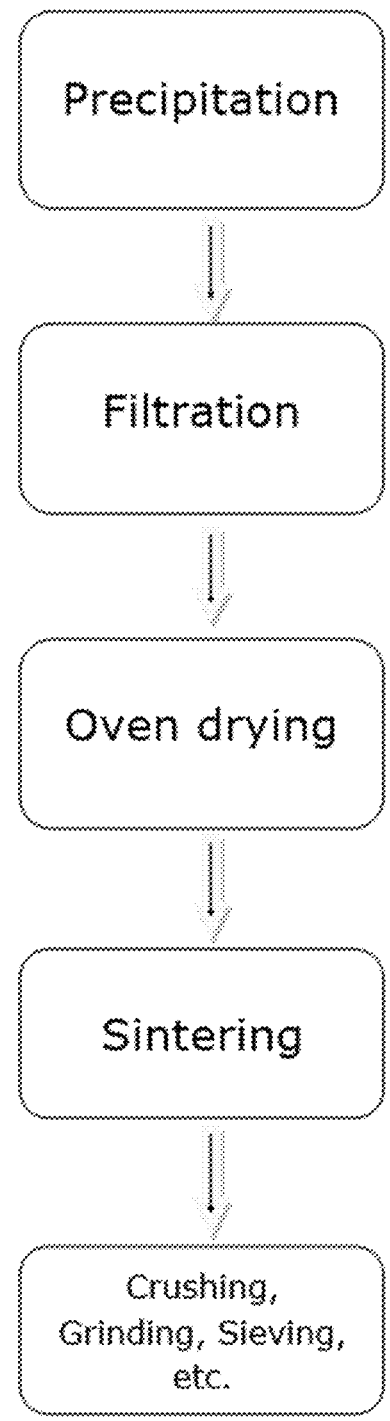

If precipitation reaction is used, the liquid is removed and the precipitate may be filtered before it is dried and finally sintered at high temperature, such as above 900° C., preferably between 900 and 1350° C. The sintered hydroxyapatite then needs to be crushed and grinded/milled and may be also sieved in order to achieve the proper particle size distribution of the raw HA powder. FIG. 4 illustrates the different steps in one way of producing raw HA.

DRAWINGS

FIG. 1 shows the fraction of CSH hydrated as a function of time. Taken from N. B. Singh and B. Middendorf, *Calcium sulfate hemihydrate hydration leading to gypsum crystallization*, Progress in Crystal Growth and Characterization of Materials 53 (2007) 57-77.

Figure 2:
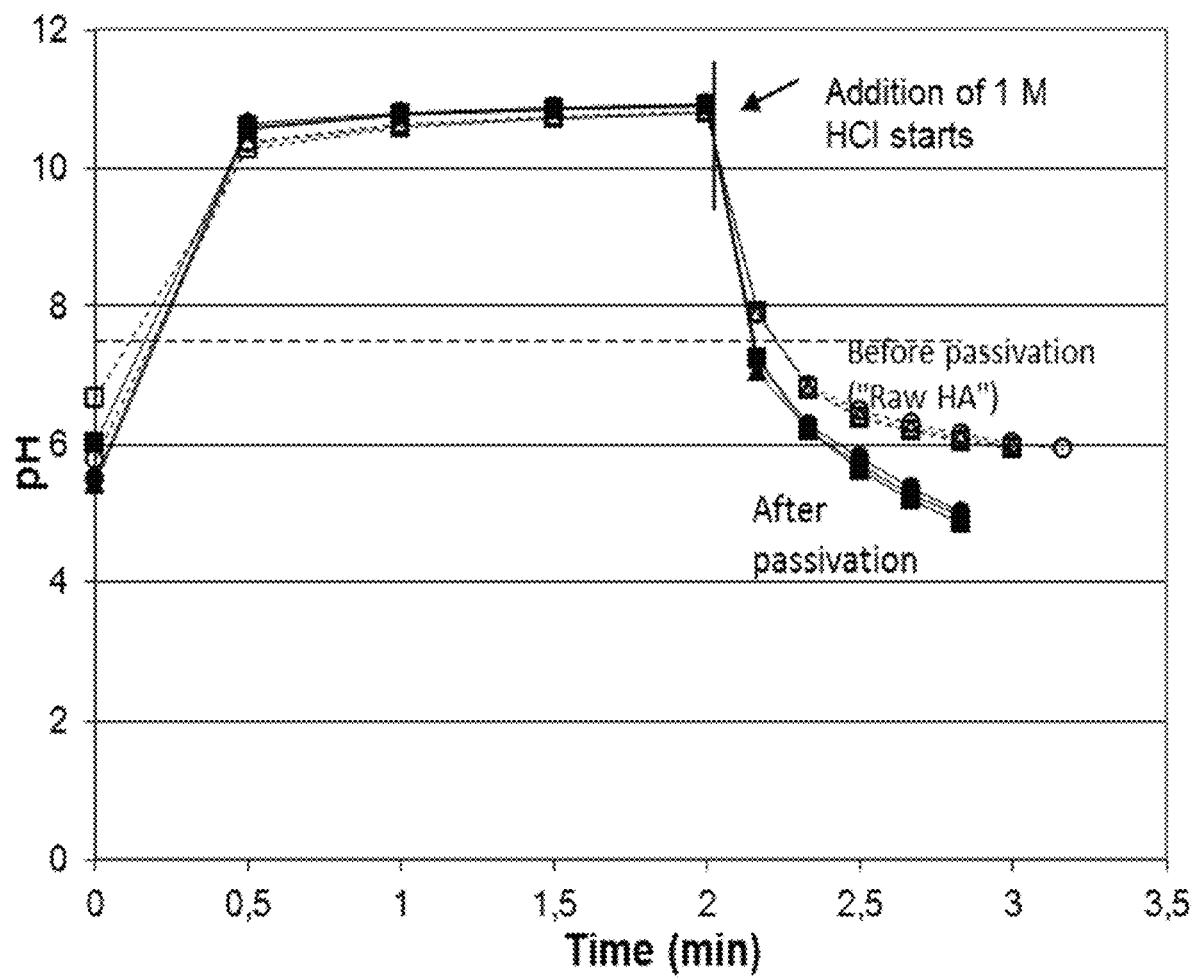

FIG. 2 shows change in buffering capacity after passivation of the HA. The dotted lines (and unfilled symbols) represents the pH/buffering results of the HA lot before passivation (raw HA). The full line (and filled symbols) represent the results of the same HA lot after passivation.

Figure 3:
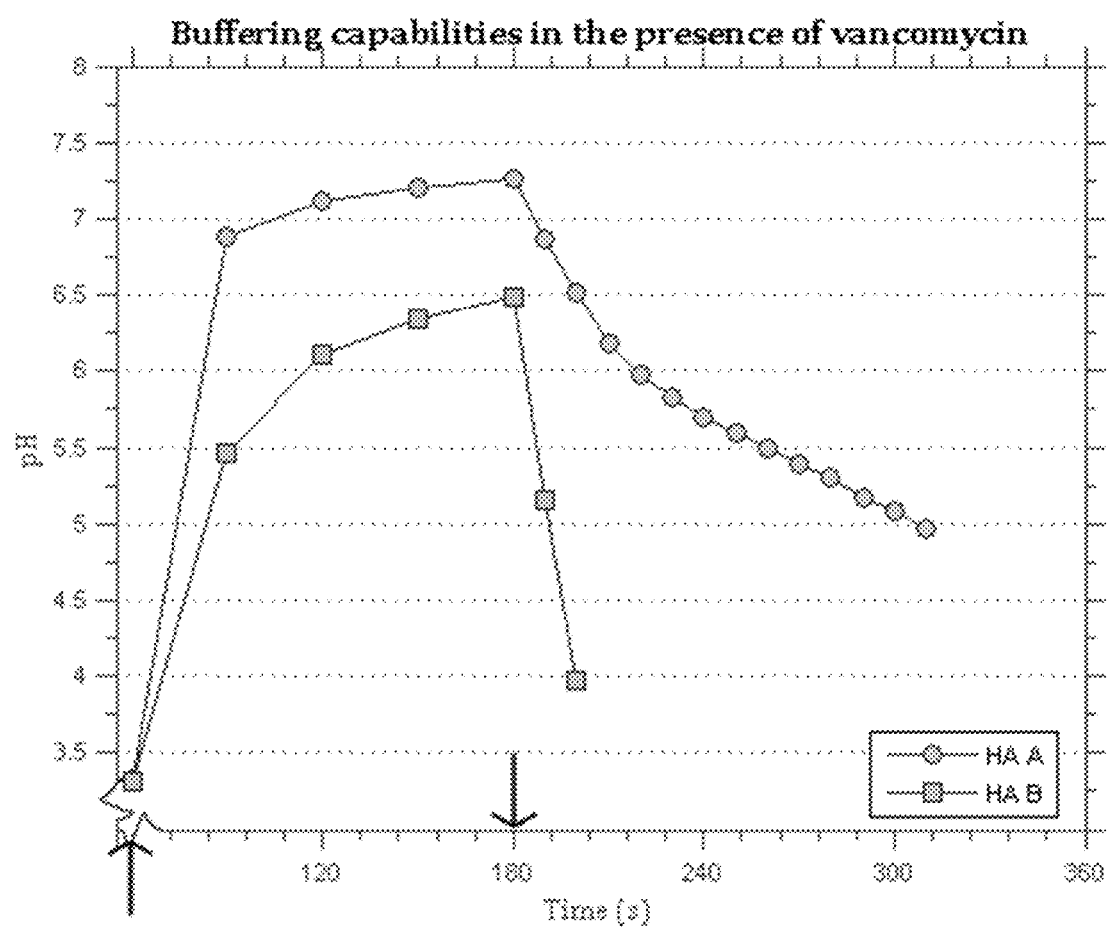

FIG. 3 shows buffering capabilities in the presence of vancomycin. HA A is before passivation (raw HA) and HA B is after passivation. Up arrow indicates when HA was added and down arrow indicates when the addition of HCl started.

FIG. 4 shows a schematic figure of the procedure for manufacturing hydroxyapatite by wet precipitation method.

DETAILED DESCRIPTION OF THE INVENTION

In describing the embodiments of the present invention, specific terminology will be used for the sake of clarity. However, the invention is not intended to be limited to the specific terms so selected, and it is understood that each specific term includes all technical equivalents which operate in a similar manner to accomplish a similar purpose.

The inventors have found out that the non-setting component hydroxyapatite (HA), which does not undergo re-crystallization in the same manner as calcium sulfate hemihydrate (CSH), and which could therefore reasonably be expected to be inert in the setting process of the calcium sulfate, apparently affects the setting time to a certain extent as described here and in the examples below.

When hardenable bone substitutes based on CSH and HA powders are produced as disclosed in the prior art, identical compositions, with the only difference being that the raw (sintered) HA component comes from different batches/lots, may give completely different setting times, even when the raw HA have similar particle size distributions and specific surface areas. An example of this observation is shown in Example 1. Due to the spread in setting time results when mixing CSH with HA, prior to the present invention, pre-testing of all potential HA lots from a supplier had to be performed before specific lots with suitable setting properties could be selected and purchase in larger quantities.

In practice, this meant that small quantities of a large number of available HA lots from the same or different producers had to be tested for their setting properties in a CSH/HA bone substitute composition, as described in Example 1, and only lots which fulfill the performance requirements (acceptable setting times) were purchased in larger quantitates for use in reliable bone substitute products. This also meant that only about 3-4 out of 10 tested lots of raw HA could be used with an acceptable, but still fluctuating, setting time in bone substitute compositions without additives.

The difference is even more pronounced when other substances are added to the CSH/HA composition, such as when antibiotics are added. By introducing additives, two compositions with roughly the same setting times without the additive may, after the additive is introduced, set at very different rates, with one system maintaining clinically relevant setting times and the other showing a setting time which is too slow to be clinically acceptable or even where a complete CSH hydration is excluded. An example of the dependence of a HA lot on the variation in setting times in systems comprising the antibiotic, vancomycin hydrochloride, is shown in Example 2. When such further additive, e.g. antibiotics, are to be mixed in the bone substitute, only a small number of HA lots tested, i.e. only 1 or less out of 10 tested lots, could be used with a satisfactory setting results. It has also been found out that additives, such as antibiotics, that do not have a retarding effect on the CSH hydration in a system containing only calcium sulfate and an aqueous liquid gives clinically unacceptable long setting times in the same system when HA is present. This is illustrated in Example 3. The critical role of HA for the setting times of calcium sulfate containing bone substitute is surprising since the calcium sulfate, and not the HA, is the setting component. Previously, the HA has been considered to be "inert" and therefore not involved in any steps of the CSH hydration reaction described above.

When comparing a hardenable bone substitute based on CSH as the setting component, and passivated HA and raw HA that has not been passivated, respectively, as a non-setting component, it is seen (Example 4) that there is a significant reduction in the setting times of such hardenable bone substitutes when passivated HA is used instead of raw HA.

The reduction in setting times from passivating the HA before use is even more pronounced when additives, such as antibiotics, are present in the CSH/HA composition. This is shown in Examples 9-11.

Accordingly the present invention relates to hardenable bone substitutes comprising as the two major components passivated crystalline HA and CSH, where the bone substitute shows a faster setting time after passivation of the crystalline HA.

Passivation of Hydroxyapatite

It is desirable that HA present in the powders of the present invention have a slow resorption rate inside the body. In order for the HA to have slow resorption the solubility of the HA should be as low as possible. The solubility is mainly determined by the stoichiometry and the crystal size. When preparing HA for use in CSH-based hardenable bone substitute, naturally occurring or synthetically produced hydroxyapatite powder is sintered at temperatures above 900° C., for example at a temperature between 900 and 1350° C. During this sintering process the crystal size of the HA will increase, which will decrease its solubility. After the sintering process, mechanical treatment of the HA material (such as any suitable type of micronization) is often necessary in order to obtain a HA powder with the right particle size distribution for use in a paste with a suitable performance. The sintered HA powder should contain >90% crystalline HA, preferably 95% or more, such as 99%. The term "crystalline hydroxyapatite" when used in the present context thus means that the sintered HA consists of >90% crystalline HA, preferably 95% or more, such as 99% crystalline HA.

It has surprisingly been found that mechanical treatment of sintered HA, to obtain powdered raw HA with the right particle size distribution, results in a retarding effect on the setting process of a CSH-based bone substitute paste, where CSH is the setting component undergoing a hydration reaction during setting, and the powdered raw HA is used as a solid non-setting component not undergoing a hydration reaction during setting. This is shown in Example 5.

The inventors have surprisingly now found that "passivating" the sintered and mechanically treated crystalline HA (raw HA) by heating it for a certain time dependent on the chosen temperature, repeals the effect of the mechanical treatment, as e.g. shown in Example 5.

Accordingly, in one aspect of the present invention, there is provided a method for preparing passivated sintered crystalline hydroxyapatite (pHA) powder as well as the products obtainable by such method, the method comprising providing a first sintered crystalline raw HA powder (for example a commercial available HA powder) and heating said powder at a temperature up to about 900° C. for at least 5 minutes to obtain said passivated HA powder. Preferably, the temperature is from 100° C. to 900° C. for between 10 minutes and 2 weeks, from 300° C. to 900° C. for between 10 minutes and 10 hours, from 300° C. to 600° C. for between 1 and 4 hours. In a particular embodiment the heat-treatment is from 450° C. to 550° C. for between 1% and 2% hours, such as 500° C. for 2 hours.

The HA powder, raw or passivated, has a crystalline content of >90%, preferably >95%, such as >99% after the sintering process, which takes place at a temperature above 900° C., for example between 900 and 1350° C. After micronization, the powder has a particle size of D(v,0.99) <1000 μm, such as <200 μm, preferably <100 μm and more preferably <50 μm, such as less than 35 μm. The specific surface area of the powder should preferable be below 20 $m^2/g$, and more preferably below 10 $m^2/g$, when measured according to the BET (Brunauer, Emmett and Teller) method, which is a method for the determination of the total surface area of a powder expressed in units of area per mass of sample ($m^2/g$) by measurement of the volume of gas (usually $N_2$) adsorbed on the surface of a known weight of the powder sample. Other ways of determining the surface area may be applied in the alternative.

The temperature and duration of the heating step necessary for passivation may be influenced by several parameters including, but not limited to, the previous sintering conditions, how extensive the mechanical treatment has been, the type and means for micronization, the crucible used during passivation heating, how much powder to be passivated and how fast the oven reaches its passivation temperature and cools off. For example, in some cases the duration and/or temperature may be reduced if the mechanical treatment has not been extensive.

It is possible by routine experimentation to determine the temperature and duration of the heating step so that it is sufficient to passivate the mechanically treated HA powder according to the present invention. One suggestion of such a routine experiment that may be applied to a HA that gives clinically irrelevant setting times when used in CSH/HA bone substitutes is the following: fractions of this HA are heat-treated at different temperatures and for different times, starting with low temperatures and/or short heat-treatment times and going towards higher temperatures and/or longer treatment times. By measuring the setting time after each heat-treatment, it is easy to judge when a higher temperature and/or a longer treatment no longer gives a further reduction in the setting times or when the HA is passivated enough to give setting times that suit the application.

The minimum duration of the heating step in the passivation can be experimentally determined, and depends on many factors, such as the temperature during passivation, the heating temperature during sintering and extent of mechanical treatment. In some embodiments the duration of the passivation heat-treatment is at least 5 minutes, such as at least 10 minutes, and preferably at least 1 hour. Preferably, the heating time is between 1 and 4 hours.

The passivation occurs faster the higher the temperature. Thus in some embodiments of the present invention, in order to reduce passivation time, the heat-treatment step is performed above 100° C., such as above 200° C., above 300° C., above 400° C., or above 500° C.

It has been found that prolonged heat-treatment of the raw HA at around 900-1000° C. and higher may cause undesired changes of properties of the HA, such as an increase in pH and/or give an alkaline buffering effect of the passivated HA in aqueous environments that was not seen before the heat-treatment. Further, such high temperatures may lead to agglomeration of the crystals leading to a need for renewed micronization and passivation steps. Thus, to maintain critical properties of the HA, such as pH in aqueous solutions after passivation, the passivation heat-treatment preferably is below 900° C., such as below 800° C. or below 700° C. In order to avoid any undesired properties of the passivated HA, it may be advantageous to use a temperature as low as practically applicable without an undesirable long heating time. Example 8 shows the effect of the heating temperature in passivation and the risk of having a too high temperature on the pH/buffering properties. Preferably, the passivation temperature is between 300 and 600° C.

It has also been found that the HA powder is less buffering after the passivation than before. Two examples that show this, with and without additives, are shown in Example 6. This effect may be used to monitor the passivation effect of the heat treatment.

All permutations of ranges involving heating time and temperature can be envisaged based on the present description, as well as repeating the heating step more than one time, for instance repeating the heating step 1, 2, 3 or 4 times or more.

Specific examples of heating steps are described in the Examples 4, 7 and 8. In some embodiments of the present invention, the heating step is e.g. from 100° C. to 900° C. for between 10 min and 2 weeks, e.g. from 200° C. to 800° C. for between 10 min and 1 week, e.g. from 300° C. to 700° C. for between 10 min and 1 week, e.g. from 400° C. to 600° C. for between 10 min and 1 week, e.g. from 450° C. to 550° C. for between 10 min and 1 week.

In some embodiments, the heating step is e.g. from 100° C. to 900° C. for between 10 min and 1 week, e.g. for between 1 h and 24 h. In some embodiments the heating step is e.g. from 300° C. to 600° C. for between 1 h and 4 h, e.g. from 400° C. to 600° C. for between 1 h and 4 h, e.g. from 450° C. to 550° C. for between 1% h and 2% h, e.g. 500° C.±10° C. for 2 h±15 min In a particular embodiment, the passivated HA is further characterized by a method where the pH/buffering capacity is investigated by studying how the pH of the HA/water solution is changed when 100 μl 1 M HCl is added every $10^{th}$ second to the suspension.

As earlier explained it has been found that prolonged treatment at around 900-1000° C. and higher may cause an alkaline buffering effect that is unwanted in some applications because it has been shown that an alkaline pH with buffering capacities may cause hemolysis and/or denature proteins and is therefore undesired in clinical applications. See Example 8.

As discussed above, different lots of sintered and micronized sintered raw HA possess different properties, dependent on the content, origin and treatment of the raw HA and therefore have different requirements for temperature/time treatment in the passivation procedure. However, for practical reasons, a standard minimum treatment could be introduced. One way of determining whether the passivation treatment has led to the desired and improved setting; i.e. a decrease in setting time, is to compare the setting time of two hardenable bone substitutes, i.e. two hardenable bone substitute pastes comprising at least CSH, HA and an aqueous phase, wherein the only difference is the HA, which in one hardenable bone substitute is a first raw HA and in the other hardenable bone substitute it is the same raw HA, however after being passivated, for example after 2 hours at 500° C. The comparison should be performed under identical conditions. A reduction in setting time of at least 3 minutes should preferable be obtained by use of passivated HA compared to non-passivated raw HA. One way of determine the setting time may be by use of Gillmore needles, where both the initial setting time (IST) and final setting time (FST) are determined. Reduction in setting time of less than 3 minutes may be the result of an inadequate passivation treatment of the raw HA lot or because the raw HA lot remains practically inert without any setting retarding properties being introduced during the sintering and micronization process. Dependent upon the severity and magnitude of the setting retarding properties of a raw HA lot, passivation of the lot may reduce the setting time by more than 3 minutes, such as by 5 minutes or more, or by 10 minutes or more, compared to the use of the raw HA lot without passivation.

Thus, in an embodiment of the present invention, the passivation of said first (raw) HA powder causes the setting time (both initial setting time (IST) and final setting time (FST), measured with e.g. Gillmore needles) for a hardenable bone substitute paste consisting of said passivated hydroxyapatite (pHA) powder, calcium sulfate powder and an aqueous liquid to be reduced, under identical conditions, by at least 3 minutes, such as 5 minutes or more, for example 10 minutes or more, compared to the setting time for the same paste, however comprising said first raw HA powder instead of said passivated HA powder.

Powders for Hardenable Bone Substitutes

The passivated HA (pHA) can be used in powders for hardenable bone substitutes, and consequently it is an aspect of the present invention to provide a powder, which is ready to use in a hardenable bone substitute, comprising as the two major components passivated crystalline HA (pHA) as described herein and CSH. The expression "ready-to-use" means that the powder includes passivated HA (in contrast to raw un-passivated HA, and therefore prepared for use with a high chance of leading to acceptable setting times), such that only an aqueous liquid, e.g. water, needs to be added before use in a clinical treatment, such as in treatment of a disease in supportive tissue, typically involving surgery.

The ready-to-use powder does not comprise an aqueous phase and is a dry powder. The CSH can exist in an alfa-CSH and a beta-CSH form. In some embodiments the CSH is alfa-CSH, as this crystal form often forms a stronger superstructure when mixed with an aqueous phase. In a preferred embodiment, CSH is the only component present in the powder that hardens by hydration.

CSH and passivated crystalline HA (pHA) is present as the major components in the ready-to-use powder, which means that these components are the two largest components when measured by weight percent (wt %). Accordingly, in one embodiment, the passivated crystalline HA (pHA) is present in the range of 20-80 wt % of the total weight of the powder components and the CSH is present in the range of 80-20 wt % of the total weight of the powder components.

In another embodiment for the invention, one or more accelerators are present in the ready-to-use powder, such as, e.g. in an amount of up to 10 wt % of the total weight of the powder components, which accelerator(s) will speed up the setting reaction of CSH by their presence and thus shorten the setting time. One such accelerator is calcium sulfate dihydrate (CSD). Other examples are suitable salts, for example inorganic salts, such as chloride and sulfate salts, for example sodium chloride. Preferably, calcium sulfate dihydrate may constitutes up to 10 wt %, such as up to 5 wt %, 2 wt %, or 1 wt % of the total weight of the powder components. In a particular embodiment, the powder components consists of 59.6 wt % alfa-CSH, 40.0 wt % passivated HA and 0.4 wt % calcium sulfate dihydrate.

In yet another embodiment of the present invention, the ready-to-use powder consists of passivated HA in the range of 35-45 wt % of the total weight of the powder components, CSH in the range of 55-65 wt % of the total weight of the powder components, and calcium sulfate dihydrate in the range of 0-5 wt %, preferably 0-2 wt % of the total weight of the powder components and optionally up to 10 wt % of other components/additives. Such other components/additives may include, but are not limited to bioactive agents, organic and inorganic viscosity modifiers, such as starches, alginates, cellulose derivatives, and the like, and/or additives to accelerate/retard the setting of the calcium sulfate.

Hardenable Bone Substitutes

In another aspect of the present invention, methods for preparing hardenable bone substitutes using the passivated crystalline HA according to the present invention is provided as well as the use of passivated crystalline HA according to the present invention in the preparation of a hardenable bone substitute.

The passivated crystalline HA according to the present invention and powders of the present invention comprising the passivated HA can be used in hardenable bone substitute pastes, such as for the manufacture of beads or any tailor-made forms for use in treatment of disorders of supportive tissue, or in the use as an injectable hardenable bone substitute paste for application to, e.g. injection at, the place of treatment of disorders of supportive tissue in a human or non-human patient.

Accordingly, another aspect of the present invention relates to a hardenable bone substitute paste, such as a hardenable bone substitute paste comprising the ready-to-use powder according to the present invention admixed with an aqueous liquid.

The paste according to the present invention is made by mixing an aqueous liquid, which in its simplest form is water, together with the ready-to-use powder to prepare the paste. In one embodiment, the final paste is made by adding one or more additives at different stages, such as dissolving the additive in the liquid prior to mixing with the powder and/or by delayed mixing as described in WO2011/098438, which is hereby incorporated by reference.

The mixing ratio for the powder and the aqueous phase is called the liquid-to-powder ratio (L/P). In some embodiments of the present invention, the L/P is in the range of 0.2-0.6 ml/g, such as between 0.3 and 0.5 ml/g. In a specific embodiment, the L/P ratio is 0.43 ml/g or 0.5 ml/g. A lower L/P ratio, such as between 0.2 and 0.4 ml/g can be employed to further reduce the IST and FST, however a lower L/P ratio may also reduce the injectability of the paste, something that is negative for several clinical applications.

In one embodiment of the present invention, the aqueous liquid is water, and in other embodiments the aqueous phase comprises one or more suitable salt(s), such as a chloride or a sulfate salt, for example sodium chloride, a water soluble non-ionic X-ray contrast agent, and/or one or more bioactive agents.

The addition of sodium chloride to the aqueous phase, such as 0.9 mg sodium chloride/ml liquid, acts as an accelerant of the calcium sulfate hydration, thereby contributing to a reduction in the IST/FST.

The addition of one or more water soluble non-ionic X-ray contrast agent is advantageous as it offers the possibility of monitoring the paste by X-ray during and right after the surgical procedure. Examples of suitable x-ray contrast agents are Iohexol compounds as described in WO 03/05388. Further suitable water soluble non-ionic X-ray contrast agents as well as their concentrations are given in WO 03/05388, which is hereby incorporated by reference. X-ray contrast agent is dissolved in pure water alone or together with suitable additives in the form of e.g. buffers and/or chelating agents. In one example, the liquid comprises Tris (tris(hydroxymethyl)aminomethane), HCl and calcium EDTA in addition to the X-ray agent, such as iohexol. Other similar X-ray agent additives are known in the art. A kit for forming a hardenable bone substitute paste according to the present invention may comprise, in addition to the ready-to-use powder, a liquid solution, e.g. water comprising an X-ray agent and suitable additives, in a separate container or the agent and optionally additives may be in a container for being dissolved in the liquid prior to use.

Suitable water soluble non-ionic X-ray contrast agent may be selected from iohexol, iodixanol, ioversol, iopamidol, iotrolane, metrizamid, iodecimol, ioglucol, ioglucamide, ioglunide, iogulamide, iomeprol, iopentol, iopromide, iosarcol, iosimide, iotusal, ioxilane, iofrotal, and iodecol.

As an alternative to water soluble non-ionic X-ray contrast agents, biodegradable particles comprising biocompatible and biodegradable X-ray contrast agent, as disclosed in WO 2009/081169, may be used to provide radiopacity in the bone substitute of the present invention. These particle are added to the ceramic powder prior to addition of the liquid.

Biodegradable X-ray contrast agent particles may be cleavable, preferably enzymatically-cleavable, derivatives of a physiologically tolerable organoiodine X-ray contrast agent, or the biodegradable X-ray particles may be prepared from biodegradable polymers comprising biocompatible, organoiodine X-ray compounds. The biodegradable X-ray contrast agents can be considered to be water insoluble derivatives of the corresponding organoiodine compounds in the sense that cleavage (for example by the body's esterases) releases physiologically tolerable organoiodine compounds.

One aspect of using biodegradable particles comprising biocompatible and biodegradable X-ray contrast agent is the particulate nature and limited water solubility of such organoiodine compounds. Initially after setting of the bone substitute material, the new biodegradable X-ray contrast agent will remain as intact particles in the cement matrix. Thereafter degradation of the contrast agent particles to water-soluble biocompatible organoiodine compounds will contribute to a beneficial osteoconductive, osteoinductive and resorbable macroporous structure of the bone substitute material.

Especially preferred derivatives of physiologically tolerable organoiodine compounds for use according to the invention include analogues of known ionic, non-ionic, monomeric or dimeric organoiodine X-ray contrast agents in which solubilising carboxylic groups are esterified with alcohols, hydroxyl groups are acylated (e.g. acetylated) or formed into 2,4-dioxacyclopentan-1-yl groups.

Biodegradable X-ray particles may be selected from the group comprising cleavable derivatives of diatrizoic acid, iobenguane, iobenzamic acid, iobitriol, iocarmic acid, iocetamic acid, iodamide, iodipamide, iodixanol, iodized oil, iodoalphionic acid, p-iodianiline, o-iodobenzoic acid, iodochlorhydroxyquin, o-iodohippurate sodium, o-iodophenol, p-iodophenol, iodophthalein sodium, iodopsin, iodpyracet, iodopyrrole, iodoquinol, ioglycamic acid, iohexol, iomeglamic acid, iomeprol, iopamidol, iopanoic acid, iopentol, iophendylate, iophenoxic acid, iopromide, iopronic acsid, iopydol, iopydone, iothalamic acid, iotrolan, ioversol, ioxiglimic acid, ioxalic acid, ioxilan and ipodate.

Examples of suitable biodegradable polymers for inclusion of x-ray agent are; poly(lactic acid) (PLA), poly(ε-caprolactone) (PCL), poly(glycolic acid) (PGA), poly(lactide-co-glycolide) (PLGA), poly(dioxanone), poly(glycolide-co-trimethylene carbonate), poly(vinyl alcohol) (PVA), poly(vinylpyrrolidine), poly(hydroxybutarates), poly(hydroxyvalerate), poly(sebaic acid-co-hexadecandioic acid anhydride), poly(trimethylene carbonate), poly(orthoester), poly(caprolactams), poly(acrylamides), poly(terphthalate), polyether block amides (PEBA), poly(urethane), polysaccarides like cellulose polymers, methylcellulose, carboxymethylcellulose, ethylcellulose, hydroxyethylcellulose, hydroxypropylmethylcellulose, natural polymers like alginates, chitosans, gelatines etc. Polymer blends, alloys, homopolymers, random copolymers, block copolymers and graft copolymers may also be suitable.

Bioactive Agents as Additives

The addition of bioactive agents to the powder or aqueous phase will be able to give the hardenable bone substitutes further beneficial properties. In an embodiment of the present invention, one or more bioactive agent(s) is/are added to the aqueous phase, and in some embodiments these bioactive agents are selected from the group consisting of: antibiotics (including antifungal drugs), chemotherapeutics, vitamins, hormones, cytostatics, bisphosphonates, growth factors, proteins, peptides, bone marrow aspirate, platelet rich plasma and demineralized bone. Silica, zirconium, strontium, and the like may be added to promote bone healing. Addition of bioactive agents to the hardenable bone substitute will result in a localized depot formulation, in which the bioactive will be released over time as. In another embodiment of the present invention, one or more bioactive agent(s) is/are added to the ready-to-use powder prior to or at the time of mixing with the liquid. The different agents may also be applied to different phases and/or at different times. A kit for forming a hardenable bone substitute paste according to the present invention may comprise, in addition to the ready-to-use powder, one or more containers containing the bioactive agent(s) to be added to the liquid solution prior to use or to the paste during use.

When the bioactive agent is an antibiotic, the hardenable bone substitute may be effective in preventing or treating osteomyelitis. There is a great interest for adding antibiotics to bone substitutes in order to prevent bone infections in treated patients. As discussed above, previous tests in the laboratory have however shown that the addition of antibiotics affects the properties of the paste significantly, mainly by a prolonged setting time. To shorten the setting time of these pastes, the use of passivated crystalline HA according to the present invention has proven to be effective.

Accordingly, in some embodiments of the present invention, antibiotic agent(s) belonging to the following groups may advantageously be part of the hardenable bone substitute according to the present invention: the group consisting of aminoglycoside antibiotics, the group consisting of penicillins, the group consisting of cephalosporins, rifampicin, clindamycin and the group consisting of antifungal drugs. Preferably, the antibiotic agent(s) is/are selected from the list consisting of: gentamicin, vancomycin, tobramycin, cefazolin, rifampicin, clindamycin, nystatin, griseofulvin, amphotericin B, ketoconazole and miconazole. One of the advantages of incorporating an antibiotic in the hardenable bone substitute paste according to the present invention is that a localized depot formulation is formed, with a much higher local concentration of the antibiotic than would be possible by systemic treatment with the same antibiotic.

In a specific embodiment of the present invention, the aqueous phase comprises the antibiotic agent gentamicin sulfate, vancomycin hydrochloride and/or cefazolin. For these antibiotic agents, the hardenable bone substitutes according to the present invention (ie with passivated HA) have been shown to give a reduction in the IST and FST (see Examples 9, 10 and 11) compared to applying these antibiotic agents in a hardenable bone substitute without passivated HA according to the present invention.

In a further aspect of the present invention the passivated HA according to the present invention is comprised in a ready-to-use hardenable bone substitute powder according to the present invention, which powder, after being mixed with a liquid is ready for use in clinical treatment, e.g. as part of a surgical treatment, in order to treat disorders of supportive tissue in a human or non-human subject by regenerating lost bone tissue and/or treating bone infections. Such disorders may be bone loss, bone fracture, bone trauma and/or osteomyelitis.

Kits for Preparing Hardenable Bone Substitutes

The ready-to-use bone substitute powders according to the present invention as well as the one or more aqueous liquids for use in the preparation of the bone substitute paste can advantageously be provided as a kit, which is ready for use and requires a minimum of handling of the various components so as to obtain an optimal time and viscosity window for applying the hardenable bone substitute in form of an injectable paste to the patient and in order to minimize the introduction of bacteria from the surroundings.

Accordingly, the present invention provides in another aspect of the invention a kit for preparing a hardenable bone substitute, comprising a ready-to-use powder according to the present invention placed in a combined mixing and injection device. Such combined mixing and injection devices (CMI devices) are known in the prior art, e.g. from WO 2005/122971. In one embodiment, the kit additionally comprises in one or more separate container(s), one or more aqueous solution(s) optionally comprising one or more accelerants and/or one or more bioactive agent(s) and/or one or more non-ionic X-ray contrast agent(s); and optionally instructions for use of said mixing and injection device. The accelerant(s), bioactive agent(s) and/or non-ionic X-ray contrast agent(s) or biodegradable X-ray particles may be included in the kit in separate containers. The kit may also comprise a combined mixing and injection device.

When describing the different aspects and embodiments of the present invention, all possible combinations and permutations of these embodiments have not been explicitly described. Nevertheless, the mere fact that certain measures are recited in mutually different dependent claims or described in different embodiments does not mean that any other combinations of these measures are not included in the present invention. The present invention envisages all possible combinations and permutations of the described embodiments.

EXAMPLES

Materials and Methods
Specifications of Raw Materials According to Standards
Powders All HA samples used in the examples have been produced by a precipitation reaction and have met the specification ASTM F 1185 "Standard Specification for Composition of Hydroxylapatite for Surgical Implants" and ISO 13779-1 "Implants for surgery—Hydroxyapatite—Part 1: Ceramic hydroxyapatite".

The purities of CSH and CSD used in the examples met the test requirements stated both in the monograph "Calcium Sulfate Dihydrate" 0982, European Pharmacopoeia and in the "Official Monograph for Calcium Sulfate" U.S. Pharmacopoeia/National Formulary.

Liquid Phase

In the Examples, either iohexol solutions (of different concentrations) or saline have been used as the liquid phase.

The iohexol solutions used consist of water for injection (WFI), Iohexol, the buffer Trometamol (Tris: tris(hydroxymethyl)aminomethane), the chelating agent Edetate Calcium Disodium (calcium EDTA) and Hydrochloric acid (HCl). The iohexol solutions meet the requirements stated in the US Pharmacopoeia for Iohexol Injection. In addition, the content of iohexol, trometamol and sodium calcium edetate meets each specific requirement according to standards.

The saline solution consists of 0.9 wt % NaCl in water for injection (WFI). The unit meets the requirements stated in the Ph EP 0193 Sodium Chloride.

The reason for having a solution comprising iohexol or similar X-ray agent as the liquid phase is to increase the radiopacity of the bone substitute material (see WO 03/053488).

Reference Powder for a Hardenable Bone Substitute

The powder for the hardenable bone substitute used in the presented examples consisted of 59.6 wt % α-CSH, 0.4 wt % CSD and 40.0 wt % HA, but the L/P ratio and type of liquid used to mix the samples varied.

Measuring Initial and Final Setting Times

The setting times were measured with Gillmore needles according to a method based on ASTM C266. After the paste for the hardenable bone substitute was prepared, some of it was transferred into three circular molds (0=10 mm, h=5 mm) and the surface was flattened. The two needles of Gillmore needles exert a pressure of 0.3 and 5 MPa respectively and the 0.3 MPa needle is placed on a regular basis (approximately once per minute) on the samples until it no longer leaves a mark. The time point when the 0.3 MPa needle does not leave a mark on the surface of the material in the molds is denoted as Initial setting time, IST. Thereafter the same procedure is repeated with the 5 MPa needle and the time point when neither this needle leaves a mark is denoted as the Final setting time, FST.

pH Measurement and Buffering Capacity Test

The method used to investigate the buffering capacity of the HA powders were based on that a slurry with 3.2 g HA powder in 32 g water was prepared. After the HA was mixed with water, 100 μl 1 M HCl was added every 10 seconds under continuously stirring. The pH was measured and noted during the whole procedure and the pH value right before the HCl additions started was denoted as the pH of the HA. If the HCl was to be added in pure water, a rapid decrease in pH could be expected, but the presence of HA powder will delay the decrease to different extents.

Example 1—Differences in Setting Behavior of CSH/HA Bone Substitute Depending on HA Lot-to-Lot Variations In this study 7 different HA lots from the same producer of HA were evaluated. All lots had been produced by sintering at 1275±50° C. for 4 h and thereafter micronized. The particle size distribution and specific surface area were similar for the 7 HA lots (mean particle size: ~5 μm and SSA: ~1.5-2 m2/g). These different lots of HA were used to prepare a CSH/HA bone substitute material.

A mixture of 59.6 wt % of synthetically produced CSH (particle size distribution: 0.1-80 μm and mean particle size ~9 μm), 40.0 wt % raw HA (different lots from same producer, see above) and 0.4 wt % of the accelerator CSD (synthetic: particle size distribution: 0.1-55 μm) were mixed with a liquid phase containing iohexol (180 mg I/mL). 30 g of the ceramic powder mixture was mixed with 15 mL iohexol solution (i.e. a liquid-to-powder ratio of 0.5 mL/g). The mixing was conducted for 30 seconds using a specially designed mixing and injection device (WO 2005/122971). The setting behavior of the obtained paste was evaluated using Gillmore needles (ASTM C266).

The results in the table below show that the setting performance of CSH/HA bone substitute can vary widely depending on the HA lots used, even if no difference can be observed between the lots by ordinary chemical/physical analyses. As can be seen, the setting times of the bone substitute are retarded significantly by using a specific HA lot, from an initial setting time (IST) of 9 min up to 56 minutes depending on the HA lot used.

| Comprised HA lot | IST/min | FST/min |
| --- | --- | --- |
| 1 | 56 ± 0 | 107 ± 2 |
| 2 | 9 ± 0 | 23 ± 2 |
| 3 | 21 ± 0 | 41 ± 0 |
| 4 | 29 ± 0 | 65 ± 0 |
| 5 | 31 ± 0 | 65 ± 0 |
| 6 | 20 ± 0 | 52 ± 1 |
| 7 | 17 ± 0 | 43 ± 6 |

Example 2—Extended Variations in Setting Behavior of CSH/HA Bone Substitutes when Antibiotics are Present In this study 3 different raw HA lots (A-C) from the same producer were selected after an initial pre-test as described in example 1, since the resulting CSH/HA bone substitute gave acceptable setting results. All lots had been produced by sintering at 1275±50° C. for 4 h and thereafter micronized. The particle size distribution and specific surface area were similar for the 3 HA lots (mean particle size. ~5 µm and SSA: ~1.5-2 m2/g).

The goal with the study was to evaluate the effect on the setting time of the CSH/HA bone substitute, containing different HA lots, when the antibiotic vancomycin was added to the system. 500 mg vancomycin (as vancomycin hydrochloride) was dissolved in the liquid phase prior to mixing with the ceramic powders.

A mixture of 59.6 wt % synthetically produced CSH (particle size distribution: 0.1-80 µm and mean particle size ~9 µm), 40.0 wt % raw HA (different lots from the same producer, see above) and 0.4 wt % of the accelerator CSD (synthetic: particle size distribution: 0.1-55 µm) were mixed with a liquid phase containing iohexol (180 mg I/mL). 18.5 g of the ceramic powder mixture was mixed with 8 mL liquid (either pure iohexol solution or iohexol solution premixed with vancomycin, see above), which gave a liquid-to-powder ratio of 0.43 mL/g). The mixing was conducted for 30 seconds using a specially designed mixing and injection device (WO 2005/122971). The setting behavior of the obtained paste was evaluated using Gillmore needles ASTM C266.

The table below shows the setting time with and without addition of ancomycin hydrochloride for three CSH/HA-compositions.

| Comprised HA lot | No antibiotics added | | 1.7* wt % vancomycin HCl | |
|---|---|---|---|---|
| | IST/min | FST/min | IST/min | FST/min |
| A | 10.5 ± 0.6 | 20.2 ± 1.5 | 12.0 ± 0 | 18.7 ± 1.2 |
| B | 14.2 ± 1.4 | 24.9 ± 1.5 | >60 | >60 |
| C | 10.9 ± 0.7 | 21.3 ± 2.4 | >60 | >60 |

*1.7 wt % based on the weight of the paste. 2.7 wt % vancomycin HCl based on the weight of the powder.

As can be seen, there is a major difference in the setting times of the CSH/HA bone substitutes as vancomycin Hydrochloride was added depending on what lot of raw HA that was used. It was shown that with no antibiotic added, the 3 different systems (with different raw HA lots) gave similar setting performance. The three lots of raw HA had been selected after an initial pre-test as described in Example 1 and without antibiotic added, all three lots of raw HA gave acceptable result. With the antibiotic present, only one of the three raw HA lots gave acceptable setting performance. For two of the systems the setting was strongly retarded and the initial setting time had not been reached within 1 hour.

Example 3 Effect of the HA on the CSH Hydration in Systems Containing Antibiotics In order to evaluate the effect of the sintered crystalline raw HA for the setting performance of CSH, two different types of bone substitutes were prepared; one with raw HA present and one without HA. Tests were performed with and without antibiotics (vancomycin or gentamycin sulfate) added to the two types of bone substitutes. The HA lot was selected after an initial pre-test as described in Example 1 and without antibiotic added, the HA lot gave an acceptable setting result for the CSH/HA bone substitute.

18.5 g ceramic powder was mixed with 8 mL iohexol solution (ie a liquid-to-powder ratio of 0.43 mL/g) with an iodine concentration of 180 mg I/mL. The first type of ceramic bone substitute consisted only of a mixture of 99.3 wt % synthetically produced CSH (particle size distribution: 0.1-80 µm and mean particle size ~7 µm) and 0.67 wt % of the accelerator CSD (synthetic: particle size distribution: 0.1-55 µm). In the second type of bone substitute raw HA was also present (59.6 wt % CSH, 40 wt % HA and 0.4 wt % CSD). The raw HA powder was commercial and had been sintered at 1275±50° C. for 4 hours and thereafter micronized. The particle size distribution was 0.1-40 µm with a mean particle size of ~7 µm.

The liquid phase contained either only the iohexol solution or iohexol solutions with 1 g of the antibiotic (either vancomycin or gentamicin sulfate) dissolved.

The mixing of the ceramic powders (either containing HA or not) and the iohexol solution (either containing the antibiotic or not) was conducted for 30 seconds using a specially designed mixing and injection device (WO 2005/122971). The setting behavior of the obtained paste was evaluated using Gillmore needles.

In the table below the setting times of the two bone substitutes with or without two different types of antibiotics are shown. As can be seen, clinically irrelevant setting times were achieved only in the cases where antibiotics were added to the composition containing HA.

Thus, the additives tested do not alone retard the setting times of the CSH but only in combination with raw HA powder. The result shows that the retarded setting obtained when antibiotics are added to the system is related to the presence of the crystalline hydroxyapatite.

| Powder phase | No antibiotics added | | 3.4* wt % Vancomycin HCl | | 3.4* wt % Gentamicin Sulfate | |
|---|---|---|---|---|---|---|
| | IST/min | FST/min | IST/min | FST/min | IST/min | FST/min |
| CSH and CSD | 4 | 10.3 | 3 | 7 | 3 | 7.2 |
| CSH, CSD and HA | 8 | 16.5 | >60 | >60 | >60 | >60 |

*The concentration is based on the paste. The concentration is 5.4 wt % based on the powder.

Example 4 Difference in Setting Times of CSH/HA Pastes Containing HA Before and after Passivation In this study 3 different HA lots (D-F) from the same producer were used. All lots had been produced by sintering at 1275±50° C. for 4 h and thereafter micronized. The particle size distribution and specific surface area were similar for the 3 HA lots (mean particle size. ~5 µm and SSA: ~1.5-2 m2/g). The three lots of HA were selected after an initial pre-test as described in Example 1 as giving unacceptable setting results of the CSH/HA bone substitute, even without antibiotic added.

Test were done in which the HA powders, were either raw HA or raw HA that had been additionally heat treated at 500° C. for 2 hours (pHA).

The ceramic powder mixture consisted of 59.6 wt % synthetically produced CSH (particle size distribution: 0.1-80 μm and mean particle size ~9 μm), 40.0 wt % HA (either raw or passivated) and 0.4 wt % of the accelerator CSD (synthetic: particle size distribution: 0.1-55 μm). The ceramic powder was mixed with a liquid phase containing iohexol (180 mg l/mL). 18.5 g of the ceramic powder mixture was mixed with 8 mL iohexol solution (ie a liquid-to-powder ratio of 0.43 mL/g). The mixing was conducted for 30 s using a specially designed mixing and injection device (WO 2005/122971). The setting behavior of the obtained paste was evaluated using Gillmore needles.

In the table below, the setting times of bone substitutes containing different HA lots before and after passivation, are presented. As can be seen, the setting times of the CSH/HA pastes containing the three lots of HA gave initial setting times in the range of 27-39 min when the HA powders has not been passivated and therefore exceed clinical relevant values. After passivation of the HA at 500° C. for 2 hours, the initial setting time decreased to approximately 10 minutes, i.e. approximately ⅓ of the initial values. All three lots of HA gave after the passivation the same (clinical relevant) performance of the bone substitute paste.

| Comprised HA lot | Before passivation | | After passivation (500° C., 2 h) | |
|---|---|---|---|---|
| | IST/min | FST/min | IST/min | FST/min |
| D | 27.1 ± 3.1 | 44.3 ± 4.6 | 9.8 ± 0.8 | 18.1 ± 1.1 |
| E | 39.0 ± 0.9 | 57.9 ± 5.4 | 8.9 ± 0.9 | 16.2 ± 1.0 |
| F | 34.4 ± 1.5 | 59.3 ± 5.2 | 10.2 ± 1.5 | 20.9 ± 1.2 |

Example 5—The Effect of the Micronization on the Retarding Effect of HA on the CSH Setting In order to further understand what causes the retardation effect hydroxyapatite has on calcium sulfate hemihydrate setting, a study was conducted with the use of a commercial hydroxyapatite powder (Riedel-de-Haën, Germany), that had not been sintered. The HA powder was sintered at 1250° C. for 3 hours at BONESUPPORT. After the sintering of the HA powder, it was treated in different ways:
Carefully crushed (particle size of some millimeters)
Ball milled (particle size <200 μm?)
Ball milled and thereafter heat treated at 360° C. for 10 h (particle size <200 μm)
Heat treated at 360° C. for 10 h and finally ball milled (particle size <200 μm)

The ceramic powder mixture consisted of 59.6 wt % synthetically produced CSH (particle size distribution: 0.1 to 80 μm and mean particle size ~9 μm), 40.0 wt % raw HA (of any of the types described above) and 0.4 wt % of the accelerator CSD (synthetic: particle size distribution: 0.1-55 μm). The ceramic powder was mixed with a liquid phase containing iohexol (300 mg L/mL). 3.0 g of the ceramic powder mixture was mixed with 1.5 mL iohexol solution (i.e. a liquid-to-powder ratio of 0.5 mL/g). The mixing of these small samples was conducted for 60 seconds using a spoon in a beaker. The setting behavior of the obtained paste was evaluated using Gillmore needles ASTM C266.

As can be seen in the table below, the HA that had been milled after the sintering and after sintering and heat-treatment step retarded the calcium sulfate setting much more than the unmilled HA and the HA that had undergone a heat-treatment after the ball milling. The results show that the ball milling step of HA causes its retarding effect on the CSH/HA bone substitute. This supports the theory that the mechanical forces applied to the HA during the milling is responsible for the retardation of the calcium sulfate.

| Treatment of the HA | IST | FST |
|---|---|---|
| Sintering at 1250° C. for 3 hours and carefully crushed | 11 min | 22 min |
| Sintering at 1250° C. for 3 h and ball milling | >2 h | >2 h |
| Sintering at 1250° C. for 3 h, ball milling, heat-treatment 360° C. 10 h | 11 min | 26 min |
| Sintering at 1250° C. for 3 h, heat-treatment 360° C. 10 h, ball milling | >2 h | >2 h |

Example 6—Change in Buffering Capacity after Passivation of the HA

Several different analysis methods were investigate in order to identify which properties of the raw HA powder were affected during the passivation step. The pH and buffering capacity were measured for the same HA lot before and after passivation. The "pH and buffering capacity test" method shows a difference when investigating the HA powders before and after the heat treatment.

In this study the pH/buffering capacity of a commercial, sintered (1275° C. for 4 hours) and micronized raw HA powder (particle size distribution: 0.1-40 μm, mean particle size ~7 μm) was analyzed, before and after passivation (i.e. heat treatment at 500° C. for 2 hours).

As can be seen from FIG. 2, the sample with the HA before passivation has a greater resistance to a change in pH when adding HCl than the sample with the passivated HA has.

The retardation effect that raw HA powders has on the setting of CSH before passivation, has been shown to be more pronounced when certain additives, such as antibiotics, are present. Therefore, the buffering capacity test was repeated with the presence of vancomycin hydrochloride (13.5 mg/ml). The results are presented in FIG. 3 and show that the difference in the resistance against the pH change caused by the HCl addition is higher for the raw HA powder before passivation (HA A) than after (HA B).

The same HA lot was used in both measurements presented, but in the first, the HA powder was passivated in 500° C. for 1 hour and in the second in 500° C. for two hours.

Example 7—Effect of Temperature for Passivation

A commercial, sintered (1275° C. for 4 h) and micronized raw HA powder (particle size distribution: 0.1-20 μm, mean particle size ~3 μm) was heat treated at different temperatures (400-600° C.) and times (1-3 hours) and then mixed in the ceramic powder mixture in order to evaluate the effect on the setting of the CSH based paste.

A ceramic powder mixture consisted of 59.6 wt % synthetically produced CSH (particle size distribution from 0.1-80 μm and mean particle size ~9 μm), 40.0 wt % HA (passivated by heating as described above) and 0.4 wt % of the accelerator CSD (synthetic: particle size distribution: 0.1-55 μm). 18.5 g of the ceramic powder mixture was mixed with 8 mL iohexol solution (180 mg l/mL), i.e. a liquid-to-powder ratio of 0.43 mL/g. The mixing was conducted for 30 seconds using a specially designed mixing and injection device (WO 2005/122971). The setting behavior of the obtained paste was evaluated using Gillmore needles.

The results in the table below show how the setting times of a calcium sulfate based bone substitute varied when the same lot of HA, but with different heat-treatments, were used. The retardering effect of the HA powder on the CSH setting time decreases when the temperature as well as the duration time of the heat treatment is increased.

| Temperature | Time | IST/min | FST/min |
|---|---|---|---|
| Before passivation | | 34.3 ± 1.0 | 61.3 ± 1.0 |
| 400° C. | 1 h | 17.1 ± 0.5 | 32.8 ± 1.0 |
| 400° C. | 2 h | 13.1 ± 0.3 | 24.4 ± 0.7 |
| 400° C. | 3 h | 10.2 ± 0.3 | 20.2 ± 0.3 |
| 500° C. | 1 h | 10.5 ± 0.8 | 21.0 ± 1.5 |
| 500° C. | 2 h | 10.1 ± 0.5 | 19.3 ± 0.6 |
| 600° C. | 3 h | 8.3 ± 0.4 | 17.0 ± 1.3 |

Example 8—the Effect the Temperature Used During Passivation Might have on the pH/Buffering Properties A commercial, sintered (1275° C. for 4 hours) and micronized raw HA powder (particle size distribution: 0.1-20 μm, mean particle size ~5 μm) was heat treated at different temperatures (between 120-900° C. for 10 hours). The lot was identified to have too long setting time properties in a test according to example 1.

After the heat treatment the different pHA samples were evaluated in the pH/buffering test. The different HA lots were also mixed into ceramic powder mixtures in order to evaluate their effect on the setting of the calcium sulfate hemihydrate.

The pH/buffering test showed that the heat treatment up to 360° C. did not affect the pH/buffering performance for this tested lot, but when the temperature was increased up to 900° C. (for 10 h) it had an effect on the powder. The HA powder which had been heat treated at 900° C. for 10 h had an increase in pH and also a higher buffering capacity (more acid had to be added to decrease the pH).

A mixture of 59.6 wt % of synthetically produced SCH (particle size distribution: 0.1-80 μm and mean particle size ~9 μm), 40.0 wt % HA (prepared as described above) and 0.4 wt % of the accelerator CSD (synthetic: particle size distribution: 0.1-55 μm) were mixed with a liquid phase containing iohexol (300 mg I/mL). 3.0 g of the ceramic powder mixture was mixed with 1.5 mL iohexol solution (i.e. a liquid-to-powder ratio of 0.5 mL/g). The mixing of these small samples was conducted for 60 seconds using a spoon in a beaker. The setting behavior of the obtained paste was evaluated using Gillmore needles.

The table below shows how the pH and buffering capacity was affected by the heat-treatment of the same HA lot from 120 to 900° C. In addition, the variation in the setting time of CSH/HA bone substitutes with a HA lot treated at the different temperatures is also shown in the table. The results showed that the retarding effect the raw HA powder has on the calcium sulfate setting time is decreased when the temperature used in the heat treatment step of the raw HA is increased. However a too high temperature (and too long time) could result in undesired properties of the HA regarding its pH/buffering properties.

| Passivation temp | Duration of pass. | pH | Amount 1M HCl needed to lower pH to 7.5 | IST/min | FST/min |
|---|---|---|---|---|---|
| Before passivation | — | 10.5 | 200 μl | 71 | >71 |
| 120 | 10 h | 10.7 | 200 μl | 39 | 70 |
| 180 | 10 h | 10.7 | 200 μl | 29 | 74 |
| 360 | 10 h | 10.5 | 200 μl | 11 | 23 |
| 900 | 10 h | 11.6 | 300 μl | 11 | 25 |

Example 9—Additions of the Antibiotic Cefazolin to CSH/HA Based Bone Substitutes Containing HA Powder Before and after Passivation In order to evaluate the effect of the raw HA for the setting performance of CSH/HA bone substitutes, two different types of bone substitutes were prepared. Both contained the same type commercial, sintered (1275° C. for 4 hours) and micronized raw HA powder (particle size distribution: 0.1-40 μm, mean particle size ~7 μm). The HA lot was selected after an initial pre-test as described in example 1, since the resulting CSH/HA bone substitute gave acceptable setting results. The HA powder was used untreated (raw HA), and after having been heat treated at 500° C. for 2 hours (i.e. passivated). The goal with this study was to investigate whether the retarding effect the antibiotic cefazolin has on CSH/HA material could be decreased if the raw HA had been passivated before mixing with the cefazolin.

The ceramic powder mixture consisted of 59.6 wt % synthetically produced SCH (particle size distribution: 0.1-80 μm and mean particle size ~9 μm), 40.0 wt % HA (either raw or passivated as described above) and 0.4 wt % of the accelerator calcium sulfate dihydrate (synthetic: particle size distribution: 0.1-55 μm). The ceramic powder was mixed with a liquid phase containing iohexol (180 mg I/mL) and 1 g of cefazolin (corresponding to 5.4 wt % of the ceramic powder phase). 18.5 g of the ceramic powder mixture was mixed with 8 mL iohexol/cefazolin solution (i.e. a liquid-to-powder ratio of 0.43 mL/g). The mixing was conducted for 30 seconds using a specially designed mixing and injection device (WO 2005/122971). The setting behavior of the obtained paste was evaluated using Gillmore needles.

The table below shows the effect of the antibiotic cefazolin on the same bone substitute system depending on whether the HA had been passivated or not. The results show that passivation of the raw HA has a large impact on the setting performance when the antibiotic cefazolin is present. Without passivation, the initial setting time was close to one hour, but decreased to <10 minutes when the raw HA powder had been passivated at 500° C. for 2 hours.

| HA | IST/min | FST/min |
|---|---|---|
| Before passivation | 53 | 61 |
| Passivated 500° C., 1 h | 7 | 11 |

Example 10—the Large Impact the Passivation of the Raw HA has on the Setting Behavior when the Antibiotic Gentamicin is Added to the CSH/HA Bone Substitute In this study 9 different raw HA lots (A-I) from the same producer were evaluated. All lots had been produced by sintering at 1275±50° C. for 4 hours and thereafter micronized. The particle size distribution and specific surface area were similar for the 9 raw HA lots (mean particle size. ~5 μm and SSA: ~1.5-2 m2/g). The HA powders were either used as raw HA or after having been heat treated at 500° C. for 2 hours (i.e. passivated). The goal with this study was to investigate whether the retarding effect the antibiotic gentamicin has on CSH/HA material could be decreased if the HA has been passivated before mixing with gentamicin.

The ceramic powder mixture consisted of 59.6 wt % synthetically produced SCH (particle size distribution: 0.1-40 μm and mean particle size ~5 μm), 40.0 wt % hydroxyapatite (either raw or passivated as described above) and 0.4 wt % of the accelerator CSD (synthetic: particle size distribution: 0.1-55 μm). The ceramic powder was mixed with a liquid phase consisting of gentamicin sulfate dissolved in saline. 6.3 g of the ceramic powder mixture was mixed with 2.7 mL of the saline/gentamicin solution (i.e. a liquid-to-powder ratio of 0.43 mL/g). 128 mg gentamicin sulfate (1.4 wt % based on the paste and 2.0 wt % based on the ceramic powder) was present in each sample.

The mixing of the small samples was conducted for 30 seconds using a spoon in the beaker. The setting behavior of the obtained paste was evaluated using Gillmore needles.

The table below shows the setting times for compositions containing the same lots and proportions of calcium sulfate, liquid and Gentamicin sulfate, but different HA lots before and after passivation at 500° C. for 2 hours. Almost all compositions gave clinically irrelevant setting times when HA without passivation was used, but after passivation, the setting times were decreased to relevant values and there were only small differences in the results no matter which lot of HA had been used. The example shows that without passivation only one of 9 lots of HA gave acceptable setting properties of this specific system with gentamicin added (acceptance criteria of initial setting ≤15 min), whereas after the passivation all 9 of the HA samples could be used. The results showed that without the use of a passivated HA the spread in setting performance is large between the CSH/HA samples containing gentamicin, but if instead a passivated HA was used the results were nearly identical and all of clinical relevance.

| Compositions with Gentamicin | Before passivation | | Passivated (500° C. 2 h) | |
|---|---|---|---|---|
| and HA lot: | IST [min] | FST [min] | IST [min] | FST [min] |
| A | 11.0 ± 0 | 15.0 ± 0 | 8.0 ± 0 | 11.0 ± 0 |
| B | 29.0 ± 1.7 | >60 | 8.0 ± 0 | 11.5 ± 0 |
| C | 27.0 ± 0 | >60 | 10.0 ± 2.6 | 19.0 ± 0 |
| D | 16.0 ± 0 | 27.0 ± 0 | 11.0 ± 0 | 15.0 ± 0 |
| E | 23.0 ± 3.5 | >60 | 8.0 ± 0 | 10.3 ± 0.6 |
| F | 37.0 ± 0 | >60 | 9.0 ± 0 | 15.0 ± 0 |
| G | 23.3 ± 2.3 | 49.0 ± 0 | 11.0 ± 0 | 15.0 ± 0 |
| H | 33.0 ± 0 | >60 | 8.3 ± 0.6 | 12.0 ± 0 |
| I | 25.0 ± 1.7 | >60 | 7.7 ± 0.6 | 12.0 ± 0 |

Example 11—the Large Impact the Passivation of the HA has on the Setting Behavior when the Antibiotic Vancomycin is Added to the CSH/HA Bone Substitute In this study 3 different raw HA lots (A-C) from the same producer of HA were evaluated. All lots had been produced by sintering at 1275±50° C. for 4 hours and thereafter micronized. The particle size distribution and specific surface area were similar for the 3 raw HA lots (mean particle size. ~5 μm and SSA: ~1.5-2 m2/g), but none of the raw HA lots could be used in the CSH/HA bone substitute if vancomycin and iohexol solution was used due to extremely long setting times (>1 hour). In this study it was investigated if a heat treatment at 500° C. for 2 hours (i.e. passivation) of the 3 different raw HA lots could enhance the setting process of the ceramic bone substitute when vancomycin was present.

The ceramic powder mixture consisted of 59.6 wt % of synthetically produced CSH (particle size distribution: 0.1-80 μm and mean particle size ~9 μm), 40.0 wt % hydroxyapatite (either raw or passivated as described above) and 0.4 wt % of the accelerator CSD (synthetic: particle size distribution: 0.1-55 μm). The ceramic powder was mixed with a liquid phase consisting of iohexol solution (180 mg I/mL) with the antibiotic vancomycin predissolved (500 mg vancomycin corresponding to 2.7 wt % of the powder weight).

18.5 g of the ceramic powder mixture was mixed with 8 mL iohexol/vancomycin solution (i.e. a liquid-to-powder ratio of 0.43 mL/g). The mixing was conducted for 30 seconds using a specially designed mixing and injection device (WO 2005/122971). The setting behavior of the obtained paste was evaluated using Gillmore needles.

The table below shows the setting times for compositions containing the same lots and proportions of CSH, CSD, liquid and vancomycin hydrochloride, but different HA lots before and after passivation at 500° C. for 2 hours. All compositions gave clinically irrelevant setting times when the raw HA was used before the passivation, but after passivation, the setting times were decreased to relevant values. The results show that if the HA is used without heat-treatment (raw HA) the setting is strongly retarded, whereas if the raw HA powder is heat treated, the setting of the CSH/HA paste is significantly shorter.

| Compositions with Vancomycin | Before passivation | | Passivated (500° C. 2 h) | |
|---|---|---|---|---|
| and HA lot: | IST [min] | FST [min] | IST [min] | FST [min] |
| A | >60 | >60 | 18.0 ± 0 | 31.0 ± 0 |
| B | >60 | >60 | 12.0 ± 0 | 23.3 ± 0.6 |
| C | >60 | >60 | 11.0 ± 0 | 18.0 ± 0 |

Example 12—Different Storage Stability of "Raw" and Passivated HA

A commercial, sintered (1275° C. for 4 hours) and micronized raw HA powder (particle size distribution: 0.1-40 μm, mean particle size ~7 μm) was investigated in the study. The powder was either used as raw HA or after additional heat treatment at 500° C. for 2 hours (i.e. passivated). The raw HA lot was selected after an initial pre-test as described in example 1, since the resulting CSH/HA bone substitute gave acceptable setting results. The two types of HA powders were placed in a humid environment (95-100% RH) at room temperature for two weeks in order to investigate the stability against moisture. Thereafter they were used in the CSH/HA bone substitute and the setting performance of the different pastes were evaluated.

The ceramic powder mixture consisted of 59.6 wt % synthetically produced CSH (particle size distribution: 0.1-80 μm and mean particle size ~9 μm), 40.0 wt % hydroxyapatite (either raw or passivated as described above) and 0.4 wt % of the accelerator CSD (synthetic: particle size 0.1-55

μm). The ceramic powder was mixed with a liquid phase consisting of an iohexol solution. 11.6 g of the ceramic powder mixture was mixed with 5 mL iohexol solution (180 mg I/mL), i.e. a liquid-to-powder ratio of 0.43 mL/g. The mixing was conducted for 30 seconds using a specially designed mixing and injection device (WO 2005/122971). The setting behavior of the obtained paste was evaluated using Gillmore needles.

The table below shows the setting times achieved for the hardenable bone substitutes before and after the HA had been stored in the humid environment. As can be seen, storage of the raw HA in a humid environment resulted in more prolonged setting times when used in the hardenable CSH/HA bone substitute compared to when passivated HA was stored and used. If the HA was not been passivated, the setting of the CS/HA paste is retarded. These results indicate that the passivated HA is more resistant towards storage.

| HA | Setting times before storage | | Setting times after storage | |
| --- | --- | --- | --- | --- |
| | IST/min | FST/min | IST/min | FST/min |
| "Raw HA" | 8.5 | 19.5 | 26.0 | 41.3 |
| Passivated HA | 6.5 | 12.0 | 9.0 | 16.0 |

Embodiments According to the Invention

1st A method for preparing a passivated crystalline hydroxyapatite powder including the steps of:
   a) providing a first hydroxyapatite powder ("raw HA");
   b) heating said first hydroxyapatite powder ("raw HA") at a temperature up to about 900° C. for at least 5 minutes to obtain a passivated hydroxyapatite powder ("passivated HA").
2nd The method according to embodiment 1, wherein the temperature in step b) is from 100° C. to 900° C. for between 10 minutes and 2 weeks, from 300° C. to 900° C. for between 10 minutes and 10 hours, from 300° C. to 600° C. for between 1 and 4 hours, preferably from 450° C. to 550° C. for between 1% and 2% hours.
3rd The method according to embodiment 1 or embodiment 2, wherein the hydroxyapatite (HA) has the chemical formula $(Ca_{10}(PO_4)_6(OH)_2)$, it does not hydrate in the presence of water and said first hydroxyapatite powder ("raw HA") has been produced by:
   1) sintering hydroxyapatite at a temperature above 900° C., for example between 900 and 1350° C., and
   2) micronizing said sintered hydroxyapatite to obtain said first hydroxyapatite powder ("raw HA").
4th The method according to any one of embodiments 1 to 3, wherein the passivated hydroxyapatite powder has a particle size D(v,0.99) <1000 μm, preferably <200 μm and more preferably <100 μm, such as <50 μm, and/or a specific surface area of <20 m$^2$/g, preferably <10 m$^2$/g as measured with BET.
5th The method according to any one of embodiments 1 to 4, wherein the passivated hydroxyapatite has a crystalline content of >90%, preferably >95%, such as >99%.
6th The method according to any one of embodiments 1 to 5, wherein the heat-treatment of said first hydroxyapatite powder ("raw HA") for 2 hours at 500° C. (ie passivation) reduces the setting time of a first hardenable bone substitute paste comprising said passivated hydroxyapatite powder, calcium sulfate powder and an aqueous liquid by 3 minutes or more (IST and FST measured with Gillmore needles), such as 5 minutes or more, or 10 minutes or more, compared to a second hardenable bone substitute paste comprising said first hydroxyapatite powder ("raw HA"), said calcium sulfate powder and said aqueous liquid in identical amounts and under identical conditions.
7th The method according to embodiment 6, wherein the setting time for the first hardenable bone substitute paste is within an acceptable range for use in clinical, including surgical, treatment.
8th A passivated hydroxyapatite powder obtainable by the method according to any one of embodiments 1-7.
9th A passivated hydroxyapatite powder according to embodiment 8 for use in a hardenable bone substitute composition further comprising calcium sulfate.
10th A passivated hydroxyapatite powder according to embodiment 9, wherein the calcium sulfate is calcium sulfate hemihydrate.
11th A passivated hydroxyapatite powder according to embodiment 9 or embodiment 10 for use in a hardenable bone substitute paste further comprising a calcium sulfate powder, such as calcium sulfate hemihydrate powder and an aqueous liquid.
12th A passivated hydroxyapatite powder according to any one of embodiments 8 to 11, wherein the hydroxyapatite $(Ca_{10}(PO_4)_6(OH)_2)$ does not react with water.
13th Use of a passivated hydroxyapatite powder obtainable by the method according to any one of embodiments 1-7 in a hardenable bone substitute composition including a calcium sulfate powder, e.g. calcium sulfate hemihydrate powder.
14th Use of a passivated hydroxyapatite powder obtainable by the method according to any one of embodiments 1-7 in a hardenable bone substitute paste including a calcium sulfate powder, e.g. calcium sulfate hemihydrate powder and an aqueous liquid.
15th A method for preparing a ready-to-use hardenable bone substitute powder comprising a hydroxyapatite powder and a calcium sulfate powder, including the steps of:
   a) providing a passivated hydroxyapatite powder,
   b) providing a calcium sulfate powder, and
   c) mixing the two powders in a suitable ratio.
16th The method according to embodiment 15, wherein the passivated hydroxyapatite powder is a powder according to any one of embodiments 8 to 12.
17th The method according to embodiment 15 or embodiment 16, wherein the ready-to-use hardenable bone substitute powder further comprises an accelerator, such as calcium sulfate dihydrate and/or a suitable salt, for example an inorganic such as a chloride or sulfate salt, for example sodium chloride.
18th The method according to any one of embodiments 15 to 17, wherein the setting time of a first hardenable bone substitute paste comprising said ready-to-use hardenable bone substitute powder and an aqueous liquid is reduced by 3 minutes or more (IST and FST measured with Gillmore needles), such as 5 minutes or more, or 10 minutes or more, compared to the setting time of a second hardenable bone substitute paste being identical to the first hardenable bone substitute paste except for the hydroxyapatite powder (from the same lot of first hydroxyapatite powder) has not been passivated ("raw HA").
19th The method according to embodiment 18, wherein the setting time (both IST and FST) of said first hardenable bone substitute paste is within a relevant range for use in clinical, including surgical, treatment.

20th A ready-to-use hardenable bone substitute powder comprising passivated hydroxyapatite powder according to any one of embodiments 8 to 12 and a calcium sulfate powder.

21st The powder according to embodiment 20, wherein the calcium sulfate powder is calcium sulfate hemihydrate powder.

22nd The powder according to embodiment 20 or embodiment 21, wherein the passivated hydroxyapatite powder is present in the range of 20-80 wt % of the total weight of the powder components and calcium sulfate hemihydrate is present in the range of 80-20 wt % of the total weight of the powder components.

23rd The powder according to any one of embodiments 20 to 22, additionally comprising an suitable amount of an accelerator, e.g. up to 10 wt %, e.g. up to 5 wt %, up to 2 wt %, or up to 1 wt % of a calcium sulfate dihydrate powder of the total weight of the powder components.

24th The powder according to embodiment 23 consisting of:
  a) 35-45 wt % passivated hydroxyapatite
  b) 55-65 wt % calcium sulfate hemihydrate
  c) 0-2 wt % calcium sulfate dihydrate, and
  d) 0-10 wt % other components.

25th A hardenable bone substitute paste comprising a ready-to-use hardenable bone substitute powder according to anyone of embodiments 20 to 24 admixed with an aqueous liquid.

26th A hardenable bone substitute paste according to embodiment 25, wherein the liquid-to-powder ratio (L/P) is in the range 0.2 to 0.6 ml/g, such as in the range 0.3 to 0.5 ml/g.

27th The bone substitute paste according to embodiment 25 or embodiment 26, wherein the aqueous liquid is water.

28th The bone substitute paste according to any one of embodiments 25 to 27, wherein the aqueous liquid comprises a suitable salt, for example an inorganic salt such as a chloride or sulfate salt, for example sodium chloride, preferably 0.9 w/v % sodium chloride.

29th The bone substitute paste according to any one of embodiments 25 to 28, wherein the aqueous liquid comprises a water soluble non-ionic X-ray contrast agent.

30th The bone substitute paste according to any one of embodiments 25 to 29, wherein the paste comprises one or more bioactive agent(s) selected from the group consisting of: antibiotics (including antifungal drugs), chemotherapeutics, vitamins, hormones, cytostatics, bisphosphonates, growth factors, bone healing promoters, proteins, peptides, bone marrow aspirate, platelet rich plasma and demineralized bone.

31st The bone substitute paste according to embodiment 30, wherein the one or more antibiotic agents belong(s) to the group of aminoglycoside antibiotics, the group of penicillin, the group of cephalosporin, the group of antifungal drugs, rifampicin or clindamycin.

32nd The bone substitute paste according to embodiment 31, wherein the antibiotic agent(s) is/are selected from the group consisting of gentamicin, vancomycin, tobramycin, cefazolin, rifampicin, clindamycin, nystatin, griseofulvin, amphotericin B, ketoconazole and miconazole.

33rd The bone substitute paste according to any one of embodiments 30 to 32, wherein the bioactive agent is mixed with the ready-to-use hardenable bone substitute powder or the aqueous liquid prior to mixing the ready-to-use hardenable bone substitute powder with the aqueous liquid, or the bioactive agent is added to the paste after mixing the ready-to-use hardenable bone substitute powder with the aqueous liquid.

34th The bone substitute paste according to any one of embodiments 25 to 33, wherein the bone substitute paste is an injectable bone substitute paste.

35th A method for preparing a hardenable bone substitute paste according to any one of embodiments 25 to 34, wherein the ready-to-use hardenable bone substitute powder is mixed with the aqueous liquid prior to use.

36th Ready-to-use hardenable bone substitute powder according to any one of embodiments 20 to 24 or hardenable bone substitute paste according to any one of embodiments 25 to 34 for use as a medicament in a clinical treatment, for example a surgical treatment.

37th Ready-to-use hardenable bone substitute powder according to any one of embodiments 20 to 24 or hardenable bone substitute paste according to any one of embodiments 25 to 34 for use in the treatment of a disorder of supportive tissues in a human or non-human subject by regenerating lost bone tissue and/or treating bone infections.

38th The ready-to-use bone substitute powder or paste according to embodiment 37, wherein the disorder is selected from conditions such as bone loss, bone fracture, bone trauma and osteomyelitis.

39th A kit for preparing an injectable hardenable bone substitute paste comprising a ready-to-use hardenable bone substitute powder according to any one of the embodiments 20 to 24, a combined mixing and injection device and optionally a suitable aqueous liquid 40th The kit according to embodiment 39 additionally comprising one or more items selected from the group consisting of one or more non-ionic X-ray contrast agent(s), one or more bioactive agent(s) such as antibiotics, antifungal drugs, chemotherapeutics, vitamins, hormones, cytostatics, bisphosphonates, growth factors, bone healing promoters, proteins, peptides, bone marrow aspirate, platelet rich plasma and/or demineralized bone, and optionally instructions, the items being contained in one or more separate containers.

41st The kit according to embodiment 40, wherein the one or more antibiotic agents belong(s) to the group of aminoglycoside antibiotics, the group of penicillin or the group of cephalosporin or the group of antifungal drugs, or rifampicin or clindamycin, preferably selected from the group consisting of gentamicin, vancomycin, tobramycin, cefazolin, rifampicin, clindamycin, nystatin, griseofulvin, amphotericin B, ketoconazole and miconazole.

42nd A method for producing a hardened bone substitute, comprising leaving the bone substitute paste according to any one of the embodiments 25 to 35 to set for a suitable period of time.

43rd A method according to embodiment 42, wherein the hardened bone substitute, such as beads or larger forms, including tailor-made forms is/are set in a mold or sculptured manually.

44th A hardened bone substitute obtainable by the method according to embodiment 42 or embodiment 43.

The invention claimed is:

1. A ready-to-use hardenable bone substitute powder comprising a calcium sulfate powder as the setting component a sintered, micronized, and passivated crystalline hydroxyapatite powder (pHA), wherein the ready-to-use hardenable bone substitute powder is prepared according to a method including the steps of:
  a) providing a sintered, micronized, and passivated crystalline hydroxyapatite (pHA) powder, by:
    (i) providing a sintered and micronized crystalline hydroxyapatite (raw HA) powder with the chemical formula $(Ca_{10}(PO_4)_6(OH)_2)$, wherein the raw HA powder has a crystalline content of >90%, a particle size below 200 μm (D(v,0.99)), and a specific surface area below 20 m²/g (BET), and (ii) heating said raw HA powder at a temperature between 300 and 900° C. for between 10 minutes and 10 hours to obtain a sintered, micronized, and passivated crystalline hydroxyapatite (pHA) powder, b) providing a calcium sulfate powder, and
c) mixing the two powders.

2. A ready-to-use hardenable bone substitute powder according to claim 1, wherein the raw HA powder is heated to between 300 and 600° C. for 1 to 4 hours.

3. A ready-to-use hardenable bone substitute powder according to claim 1, wherein the calcium sulfate powder is calcium sulfate hemihydrate powder.

4. A ready-to-use hardenable bone substitute powder according to claim 1, wherein the ready-to-use hardenable bone substitute powder further comprises an accelerator for the setting of calcium sulfate.

5. A ready-to-use hardenable bone substitute powder according to claim 4, wherein the accelerator is calcium sulfate dihydrate and/or an inorganic salt.

6. A ready-to-use hardenable bone substitute powder according to claim 5, wherein the accelerator is sodium chloride.

7. A ready-to-use hardenable bone substitute powder according to claim 1, comprising 35-45 wt % sintered, micronized, and passivated hydroxyapatite (pHA) powder, 55-65 wt % calcium sulfate hemihydrate powder of the total weight of the powder components and optionally an accelerator for the setting of calcium sulfate.

8. A ready-to-use hardenable bone substitute powder according to claim 7, comprising up to 5 wt % of an accelerator of the total weight of the powder components.

9. A ready-to-use hardenable bone substitute powder according to claim 8, wherein the powder comprises up to 2 wt % of calcium sulfate dihydrate powder of the total weight of the powder components.

10. A ready-to-use hardenable bone substitute powder according to claim 1 consisting of:
a) 35-45 wt % sintered, micronized, and passivated hydroxyapatite (pHA) powder;
b) 55-65 wt % calcium sulfate hemihydrate powder;
c) 0-5 wt % calcium sulfate dihydrate powder; and
d) 0-10 wt % other components.

11. A ready-to-use hardenable bone substitute powder according to claim 1 comprising one or more bioactive agent(s) selected from the group consisting of antibiotics, antifungal drugs, chemotherapeutics, vitamins, hormones, cytostatics, bisphosphonates, growth factors, bone healing promoters, proteins, peptides, bone marrow aspirate, platelet rich plasma and demineralized bone.

12. A ready-to-use hardenable bone substitute powder according to claim 11, wherein the antibiotic agent is selected from the group consisting of gentamicin, vancomycin, tobramycin, cefazolin, rifampicin, clindamycin and the antifungal drug is selected from the group comprising nystatin, griseofulvin, amphotericin B, ketoconazole and miconazole.

13. A ready-to-use hardenable bone substitute powder according to claim 1, further comprising biodegradable X-ray contrast agent particles.

14. A hardenable bone substitute paste comprising a ready-to-use hardenable bone substitute powder according to claim 1 admixed with an aqueous liquid.

15. A hardenable bone substitute paste according to claim 14, wherein the aqueous liquid is water, optionally comprising an inorganic salt and/or a water soluble non-ionic X-ray contrast agent.

16. A hardenable bone substitute paste according to claim 15, wherein the water soluble non-ionic X-ray contrast agent is selected from iohexol, iodixanol, ioversol, iopamidol, iotrolane, metrizamid, iodecimol, ioglucol, ioglucamide, ioglunide, iogulamide, iomeprol, iopentol, iopromide, iosarcol, iosimide, iotusal, ioxilane, iofrotal, and iodecol.

17. A hardenable bone substitute paste according to claim 14, wherein the liquid-to-powder ratio (L/P) is in the range 0.2 to 0.6 ml/g.

18. A kit for preparing an injectable hardenable bone substitute paste comprising a ready-to-use hardenable bone substitute powder according to claim 1 and optionally an aqueous liquid in separate containers, the liquid optionally comprising a non-ionic X-ray contrast agent.

19. A kit according to claim 18 further comprising one or more bioactive agent(s) selected from the group consisting of antibiotics, antifungal drugs, chemotherapeutics, vitamins, hormones, cytostatics, bisphosphonates, growth factors, bone healing promoters, proteins, peptides, bone marrow aspirate, platelet rich plasma and/or demineralized bone in one or more separate containers.

20. A hardenable bone substitute paste according to claim 17, wherein the liquid-to-powder ratio (L/P) is in the range 0.3 to 0.5 ml/g.

* * * * *

UNITED STATES PATENT AND TRADEMARK OFFICE
CERTIFICATE OF CORRECTION

PATENT NO. : 10,994,998 B2
APPLICATION NO. : 15/981501
DATED : May 4, 2021
INVENTOR(S) : Kristina Caroline Victoria Ehrenborg, Veronica Rebecca Sandell and Eva Christina Lidén Page 1 of 1

It is certified that error appears in the above-identified patent and that said Letters Patent is hereby corrected as shown below:

In the Claims

At Column 26, Line 60, "a sintered, micronized, and passivated" should read --and a sintered, micronized, and passivated--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*